(12) United States Patent
Patel et al.

(10) Patent No.: US 9,510,930 B2
(45) Date of Patent: Dec. 6, 2016

(54) ANGIOPLASTY DEVICE WITH EMBOLIC FILTER

(75) Inventors: Udayan G. Patel, San Jose, CA (US); Ravish Sachar, Raleigh, NC (US)

(73) Assignee: Contego Medical, LLC, Raleigh, NC (US)

( * ) Notice: Subject to any disclaimer, the term of this patent is extended or adjusted under 35 U.S.C. 154(b) by 363 days.

(21) Appl. No.: 12/604,236

(22) Filed: Oct. 22, 2009

(65) Prior Publication Data

US 2010/0106182 A1   Apr. 29, 2010

Related U.S. Application Data

(60) Provisional application No. 61/107,391, filed on Oct. 22, 2008, provisional application No. 61/107,395, (Continued)

(51) Int. Cl.
   *A61M 29/00* (2006.01)
   *A61F 2/01* (2006.01)
   *A61M 25/06* (2006.01)

(52) U.S. Cl.
   CPC .......... *A61F 2/013* (2013.01); *A61F 2002/016* (2013.01); *A61F 2002/018* (2013.01); *A61F 2230/0006* (2013.01); *A61F 2230/008* (2013.01); *A61F 2230/0067* (2013.01); *A61F 2230/0069* (2013.01); *A61F 2230/0093* (2013.01); *A61M 2025/0681* (2013.01)

(58) Field of Classification Search
   CPC ...... A61F 2/01; A61F 2/013; A61F 2002/011; A61F 2002/016; A61F 2002/018
   USPC .................. 606/108, 198, 200; 604/104–107
   See application file for complete search history.

(56) References Cited

U.S. PATENT DOCUMENTS

| 4,723,549 A | 2/1988 | Wholey et al. |
| 5,456,667 A | 10/1995 | Ham et al. |

(Continued)

FOREIGN PATENT DOCUMENTS

| DE | 20 2005 022 063.9 | 11/2005 |
| DE | 202005022063 U1 | 3/2013 |

(Continued)

OTHER PUBLICATIONS

Baim, D.S., et al. Randomized trial of a distal embolic protection device during percutaneous intervention of saphenous vein aortocoronary bypass grafts, Circulation, v. 105, pp. 1285-1290 (2002).

(Continued)

*Primary Examiner* — Gregory Anderson
*Assistant Examiner* — Sarah Simpson
(74) *Attorney, Agent, or Firm* — Meunier Carlin & Curfman LLC

(57) ABSTRACT

An angioplasty device has a filter associated with it to capture embolic particles that may be broken free during an angioplasty procedure. In one embodiment the embolic filter has a frame in which struts are connected to end rings and to each other by a plurality of interconnected oval members. In another embodiment the device includes an actuator at the proximal end of an actuator wire. By rotating a knob on the device, the physician can smoothly tension the wire by a predetermined amount to prevent the filter from opening too much or too little. Various other embodiments of filter frames are also disclosed.

16 Claims, 23 Drawing Sheets

Related U.S. Application Data filed on Oct. 22, 2008, provisional application No. 61/107,404, filed on Oct. 22, 2008.

(56) References Cited

U.S. PATENT DOCUMENTS

| | | | |
|---|---|---|---|
| 5,913,895 A | 6/1999 | Burpee et al. | |
| 5,954,745 A | 9/1999 | Gertler et al. | |
| 6,042,598 A | 3/2000 | Tsugita et al. | |
| 6,051,014 A | 4/2000 | Jang | |
| 6,391,044 B1 | 5/2002 | Yadav et al. | |
| 6,485,502 B2 | 11/2002 | Don Michael et al. | |
| 6,511,503 B1 | 1/2003 | Burkett et al. | |
| 6,524,303 B1 | 2/2003 | Garibaldi | |
| 6,537,297 B2 | 3/2003 | Tsugita et al. | |
| 6,592,606 B2* | 7/2003 | Huter et al. | 606/200 |
| 6,635,084 B2 | 10/2003 | Israel et al. | |
| 6,656,203 B2 | 12/2003 | Roth et al. | |
| 6,682,543 B2 | 1/2004 | Barbut et al. | |
| 6,702,834 B1* | 3/2004 | Boylan et al. | 606/200 |
| 6,866,677 B2 | 3/2005 | Douk et al. | |
| 6,929,660 B1* | 8/2005 | Ainsworth | A61F 2/91 623/1.15 |
| 6,939,373 B2 | 9/2005 | Gomez et al. | |
| 6,964,673 B2 | 11/2005 | Tsugita et al. | |
| 6,978,174 B2 | 12/2005 | Gelfand et al. | |
| 7,094,249 B1 | 8/2006 | Broome et al. | |
| 7,097,651 B2 | 8/2006 | Harrison et al. | |
| 7,137,991 B2 | 11/2006 | Fedie | |
| 7,241,305 B2 | 7/2007 | Ladd | |
| 7,338,510 B2* | 3/2008 | Boylan et al. | 606/200 |
| 7,780,696 B2 | 8/2010 | Daniel et al. | |
| 7,931,659 B2* | 4/2011 | Bose | A61B 17/22 606/113 |
| 7,935,075 B2 | 5/2011 | Tockman et al. | |
| 8,150,520 B2 | 4/2012 | Demarais et al. | |
| 8,372,108 B2 | 2/2013 | Lashinski | |
| 8,403,976 B2 | 3/2013 | Sachar et al. | |
| 8,518,073 B2 | 8/2013 | Lashinski | |
| 8,758,424 B2 | 6/2014 | Sachar et al. | |
| 2001/0012951 A1 | 8/2001 | Bates et al. | |
| 2002/0156457 A1 | 10/2002 | Fisher | |
| 2003/0004536 A1* | 1/2003 | Boylan et al. | 606/200 |
| 2003/0055480 A1 | 3/2003 | Fischell et al. | |
| 2003/0060843 A1 | 3/2003 | Boucher | |
| 2003/0065354 A1* | 4/2003 | Boyle et al. | 606/200 |
| 2003/0083736 A1 | 5/2003 | Brown et al. | |
| 2003/0093106 A1 | 5/2003 | Brady et al. | |
| 2003/0139764 A1 | 7/2003 | Levinson et al. | |
| 2003/0167084 A1 | 9/2003 | Orlowski | |
| 2003/0176884 A1 | 9/2003 | Berrada et al. | |
| 2003/0212361 A1 | 11/2003 | Boyle et al. | |
| 2003/0216792 A1 | 11/2003 | Levin et al. | |
| 2003/0220665 A1 | 11/2003 | Eskuri et al. | |
| 2003/0225435 A1 | 12/2003 | Huter et al. | |
| 2004/0054322 A1 | 3/2004 | Vargas | |
| 2004/0122466 A1 | 6/2004 | Bales | |
| 2004/0158280 A1 | 8/2004 | Morris et al. | |
| 2004/0172128 A1* | 9/2004 | Hong et al. | 623/1.16 |
| 2004/0260387 A1* | 12/2004 | Regala et al. | 623/1.15 |
| 2005/0015111 A1* | 1/2005 | McGuckin et al. | 606/200 |
| 2005/0038468 A1 | 2/2005 | Panetta et al. | |
| 2005/0119668 A1* | 6/2005 | Teague et al. | 606/127 |
| 2005/0228438 A1* | 10/2005 | Sachar et al. | 606/200 |
| 2005/0288730 A1 | 12/2005 | Deem et al. | |
| 2006/0041277 A1 | 2/2006 | Deem et al. | |
| 2006/0100658 A1 | 5/2006 | Obana et al. | |
| 2006/0129130 A1 | 6/2006 | Tal et al. | |
| 2006/0129180 A1 | 6/2006 | Tsugita et al. | |
| 2006/0142801 A1 | 6/2006 | Demarais et al. | |
| 2006/0235474 A1 | 10/2006 | Demarais | |
| 2007/0043306 A1 | 2/2007 | Olson | |
| 2007/0061418 A1 | 3/2007 | Berg | |
| 2007/0167975 A1 | 7/2007 | Boyle et al. | |
| 2007/0299466 A1 | 12/2007 | Sachar et al. | |
| 2008/0097399 A1 | 4/2008 | Sachar et al. | |
| 2010/0106182 A1 | 4/2010 | Patel et al. | |
| 2011/0071619 A1 | 3/2011 | Bliss et al. | |
| 2012/0330402 A1 | 12/2012 | Vad et al. | |
| 2013/0031087 A1 | 1/2013 | Kropitz et al. | |
| 2013/0226225 A1 | 8/2013 | Sachar et al. | |
| 2013/0310871 A1 | 11/2013 | Sachar et al. | |
| 2014/0135661 A1 | 5/2014 | Garrison et al. | |
| 2014/0214067 A1 | 7/2014 | Sachar et al. | |
| 2014/0277383 A1 | 9/2014 | Sachar et al. | |

FOREIGN PATENT DOCUMENTS

| | | |
|---|---|---|
| EP | 1951147 A2 | 8/2008 |
| HK | 09101129.3 | 11/2005 |
| JP | 2002-336261 A | 11/2002 |
| JP | 2008-542291 | 11/2005 |
| JP | 2013-049398 | 3/2013 |
| JP | 2013-154183 A | 8/2013 |
| WO | PCT/US2014/021850 | 3/2004 |
| WO | WO-2004/096089 A2 | 11/2004 |
| WO | WO-2005/004968 A1 | 1/2005 |
| WO | WO-2007/061418 A2 | 5/2007 |
| WO | WO-2009/151761 A1 | 12/2009 |
| WO | PCT/US2013/072232 | 11/2013 |
| WO | PCT/US2014/029342 | 3/2014 |
| WO | WO-2014/085590 A1 | 6/2014 |
| WO | WO-2014/144787 A1 | 9/2014 |
| WO | WO-2014/150013 A1 | 9/2014 |
| WO | WO 2015/070147 | 5/2015 |

OTHER PUBLICATIONS

"Mounted," American Webster Dictionary, http://dictionary.reference.com/browse/mounted (Jan. 28, 2007).

International Search Report and Written Opinion issued Nov. 5, 2009 for International Patent Application No. PCT/US09/040202, which was filed on Apr. 10, 2009 and published as WO 2009/151761 on Dec. 17, 2009 (Inventor—Sachar; Applicant—Contego Medical, LLC) (pp. 1-6).

International Preliminary Report on Patentability issued Oct. 12, 2010 for International Patent Application No. PCT/US09/040202, which was filed on Apr. 10, 2009 and published as WO 2009/151761 on Dec. 17, 2009 (Inventor—Sachar; Applicant—Contego Medical, LLC) (pp. 1-5).

International Search Report and Written Opinion issued Jun. 28, 2007 for International Patent Application No. PCT/US05/042826, Which was filed on Nov. 26, 2005 and published as WO 2007/061418 on May 31, 2007 (Inventor—Sachar; Applicant—Contego Medical, LLC) (pp. 1-5).

International Preliminary Report on Patentability issued May 27, 2008 for International Patent Application No. PCT/US05/042826, Which was filed on Nov. 26, 2005 and published as WO 2007/061418 on May 31, 2007 (Inventor—Sachar; Applicant—Contego Medical, LLC) (pp. 1-4).

International Search Report and Written Opinion issued Feb. 18, 2014 for International Patent Application No. PCT/US2013/072232, which was filed on Nov. 27, 2013 (Inventor—Sachar; Applicant—Contego Medical, LLC) (pp. 3-9).

Restriction Requirement issued Apr. 12, 2007 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-6).

Response to Restriction Requirement filed Jun. 12, 2007 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-13).

Non-Final Office Action issued Aug. 23, 2007 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).

Response to Non-Final Office Action filed Nov. 19, 2007 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-18).

(56) References Cited

OTHER PUBLICATIONS

Final Office Action issued Feb. 5, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-9).
Pre-Appeal Brief Request and Notice of Appeal filed Apr. 23, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-5).
Notice of Panel Decision from Pre-Appeal Brief Review issued Jun. 5, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-2).
Amendment and Request for Continued Examination filed Aug. 5, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-10).
Non-Final Office Action issued Oct. 29, 2008 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).
Non-Final Office Action issued Feb. 10, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).
Examiner Interview Summary issued Mar. 11, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-4).
Response to Non-Final Office Action filed Mar. 30, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-17).
Applicant Summary of Interview with Examiner filed Mar. 31, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-3).
Final Office Action issued Jun. 16, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).
Response After Final Office Action filed Aug. 12, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-11).
Final Office Action issued Sep. 2, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-10).
Examiner Interview Summary issued Nov. 20, 2009 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-4).
Applicant Summary of Interview with Examiner filed Mar. 1, 2010 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-8).
Response to Final Office Action filed Mar. 2, 2010 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-11).
Final Office Action issued Mar. 17, 2010 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-10).
Amendment and Request for Continued Examination filed Sep. 17, 2010 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-13).

Non-Final Office Action issued May 19, 2011 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-9).
Response to Non-Final Office Action filed Jun. 23, 2011 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-22).
Final Office Action issued Sep. 27, 2011 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-13).
Response After Final Office Action filed Nov. 29, 2011 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-19).
Advisory Action issued Jan. 11, 2012 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-3).
Response and Request for Continued Examination filed Feb. 27, 2012 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-11).
Applicant-Initiated Interview Summary issued Jan. 2, 2013 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-3).
Notice of Allowance issued Feb. 20, 2013 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-10).
Examiner-Initiated Interview Summary issued Feb. 20, 2013 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-1).
Issue Notification issued Mar. 6, 2013 for U.S. Appl. No. 10/997,803, filed Nov. 24, 2004 and issued as U.S. Pat. No. 8,403,976 on Mar. 26, 2013 (Inventor—Sachar; Applicant—Contego Medical, LLC) (pp. 1-1).
Preliminary Amendment filed Aug. 24, 2007 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-15).
Non-Final Office Action issued Jul. 16, 2009 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-11).
Response to Non-Final Office Action filed Oct. 16, 2009 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-17).
Applicant's Summary of Telephone Interview with Examiner filed Nov. 17, 2009 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-6).
Final Office Action issued Dec. 30, 2009 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-10).
Response and Request for Advisory Action filed Feb. 24, 2010 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-13).
Advisory Action issued Mar. 5, 2010 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-3).
Amendment and Request for Continued Examination filed Mar. 29, 2010 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-14).

(56) References Cited

OTHER PUBLICATIONS

Non-Final Office Action issued Jun. 8, 2010 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-10).
Response to Non-Final Office Action filed Dec. 8, 2010 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-15).
Final Office Action issued Feb. 10, 2011 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-12).
Examiner Interview Summary issued Apr. 8, 2011 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-4).
Response and Request for Continued Examination filed Jun. 23, 2011 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-19).
Non-Final Office Action issued Sep. 14, 2011 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-13).
Response to Non-Final Office Action filed Dec. 15, 2011 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-28).
Final Office Action issued Feb. 27, 2012 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-16).
Response and Request for Continued Examination filed Jun. 27, 2012 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-19).
Non-Final Office Action issued Dec. 20, 2012 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-15).
Notice of Appeal filed Jun. 20, 2013 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-2).
Notice of Abandonment issued Feb. 28, 2014 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-2).
Amendment and Response to Non-Final Office Action filed Mar. 28, 2014 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-16).
Petition for Revival of Application filed Mar. 28, 2014 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-3).
Petition Decision issued Apr. 8, 2014 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-2).
Examiner-Initiated Interview Summary issued Oct. 9, 2013 for U.S. Appl. No. 13/850,782, filed Mar. 26, 2013 and published as U.S. 2013/0226225 on Aug. 29, 2013 (Inventor—Sachar; Applicant—Contego Medical, LLC) (pp. 1-1).
Notice of Allowance issued Oct. 9, 2013 for U.S. Appl. No. 13/850,782, filed Mar. 26, 2013 and published as U.S. 2013/0226225 on Aug. 29, 2013 (Inventor—Sachar; Applicant—Contego Medical, LLC) (pp. 1-14).
Amendment and Response filed Mar. 27, 2014 for U.S. Appl. No. 13/850,782, filed Mar. 26, 2013 and published as U.S. 2013/0226225 on Aug. 29, 2013 (Inventor—Sachar; Applicant—Contego Medical, LLC) (pp. 1-6).
Response to Amendment issued Apr. 1, 2014 for U.S. Appl. No. 13/850,782, filed Mar. 26, 2013 and published as U.S. 2013/0226225 on Aug. 29, 2013 (Inventor—Sachar; Applicant—Contego Medical, LLC) (pp. 1-2).
Preliminary Amendment filed Mar. 17, 2014 for U.S. Appl. No. 14/091,903, filed Nov. 27, 2013 (Inventor—Sachar; Applicant—Contego Medical, LLC) (pp. 1-3).
Amendment and Response to Notice of Incomplete Reply filed Apr. 21, 2014 for U.S. Appl. No. 14/091,903, filed Nov. 27, 2013 (Inventor—Sachar; Applicant—Contego Medical, LLC) (pp. 1-3).
European Search Report issued Oct. 7, 2011 for European Patent Application No. 05852233.5, which was filed on Nov. 26, 2005 and published as EP 1951147 on Aug. 6, 2008 (Inventor—Sachar; Application—Contego Medical, LLC) (pp. 1-7).
Kumar et al. "Effects of Design Parameters on the Radial Force of Percutaneous Aortic Valve Stents," Cardiovasc Revasc Med. Apr.-Jun. 2010;11(2):101-4.
Non-Final Office Action issued Jan. 22, 2015 for U.S. Appl. No. 11/763,118, filed Jun. 14, 2007 and published as U.S. 2007/0299466 on Dec. 27, 2007 (Inventor—Sachar; Applicant—Contego Medical, LLC) (pp. 1-23).
Response to Non-Final Office Action filed Apr. 22, 2015 for U.S. Patent Application No. 11/763,118, filed Jun. 14, 2007 and published as U.S. 2007/0299466 on Dec. 27, 2007 (Inventor—Sachar; Applicant—Contego Medical, LLC) (pp. 1-16).
Issue Notification issued Jun. 4, 2014 for U.S. Appl. No. 13/850,782, filed Mar. 26, 2013 and published as U.S. 2013/0226225 on Aug. 29, 2013 (Inventor—Sachar; Applicant—Contego Medical, LLC) (p. 1).
International Search Report and Written Opinion issued Jul. 21, 2014 for International Patent Application No. PCT/US14/21850, which was filed on Mar. 7, 2014 and published as WO 2014/150013 on Sep. 25, 2014 (Inventor—Sachar; Applicant—Contego Medical, LLC) (pp. 1-9).
Non-Final Office Action issued Feb. 2, 2015 for U.S. Appl. No. 13/838,523, filed Mar. 15, 2013 and published as U.S. 2013/0310871 on Nov. 21, 2013 (Inventor—Sachar; Applicant—Contego Medical, LLC) (pp. 1-9).
International Search Report and Written Opinion issued Aug. 19, 2014 for International Patent Application No. PCT/US2014/029342, which was filed on Mar. 14, 2014 and published as WO 2014/144787 on Sep. 18, 2014 (Inventor—Sachar; Applicant—Contego Medical, LLC) (pp. 1-6).
Non-Final Office Action issued Mar. 5, 2015 for U.S. Appl. No. 14/213,668, filed Mar. 14, 2014 and published as U.S. 2014/0277383 on Sep. 18, 2014 (Inventor—Sachar; Applicant—Contego Medical, LLC) (pp. 1-13).
International Search Report and Written Opinion issued Feb. 23, 2015 for International Patent Application No. PCT/US2014/064817, which was filed on Nov. 10, 2014 and published as WO 2015/070147 on May 14, 2015 (Inventor—Sachar; Applicant—Contego Medical, LLC) (pp. 1-6).
U.S. Appl. No. 61/730,213, filed Nov. 27, 2012, Sachar (Contego Medical, LLC).
U.S. Appl. No. 61/794,877, filed Mar. 15, 2013, Sachar (Contego Medical, LLC).
U.S. Appl. No. 61/794,924, filed Mar. 15, 2013, Sachar (Contego Medical, LLC).
U.S. Appl. No. 14/213,668, filed Mar. 14, 2014, Sachar (Contego Medical, LLC).
U.S. Appl. No. 61/901,734, filed Nov. 8, 2013, Sachar (Contego Medical, LLC).

* cited by examiner

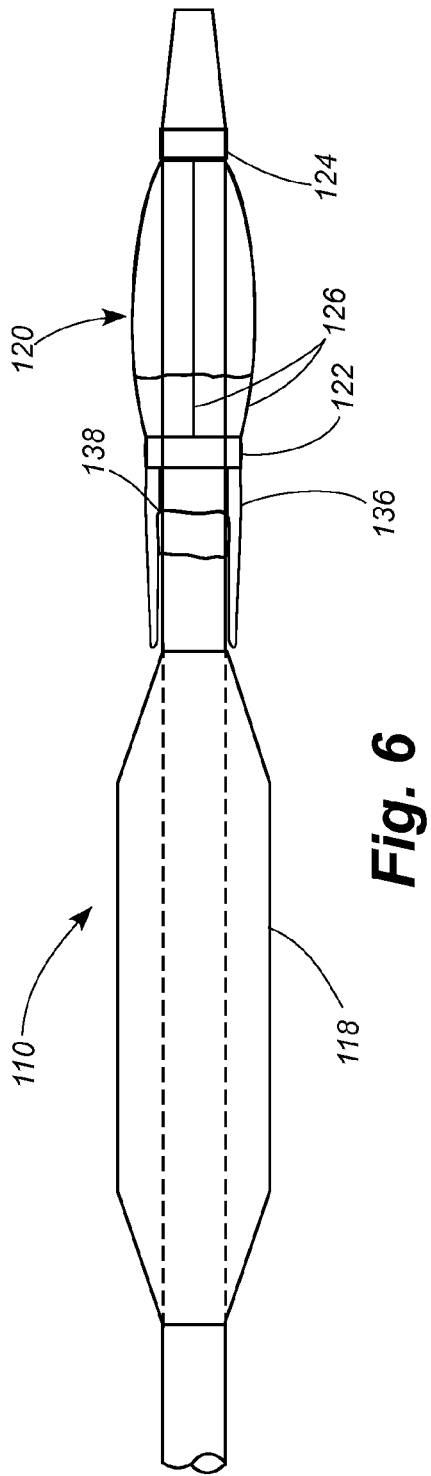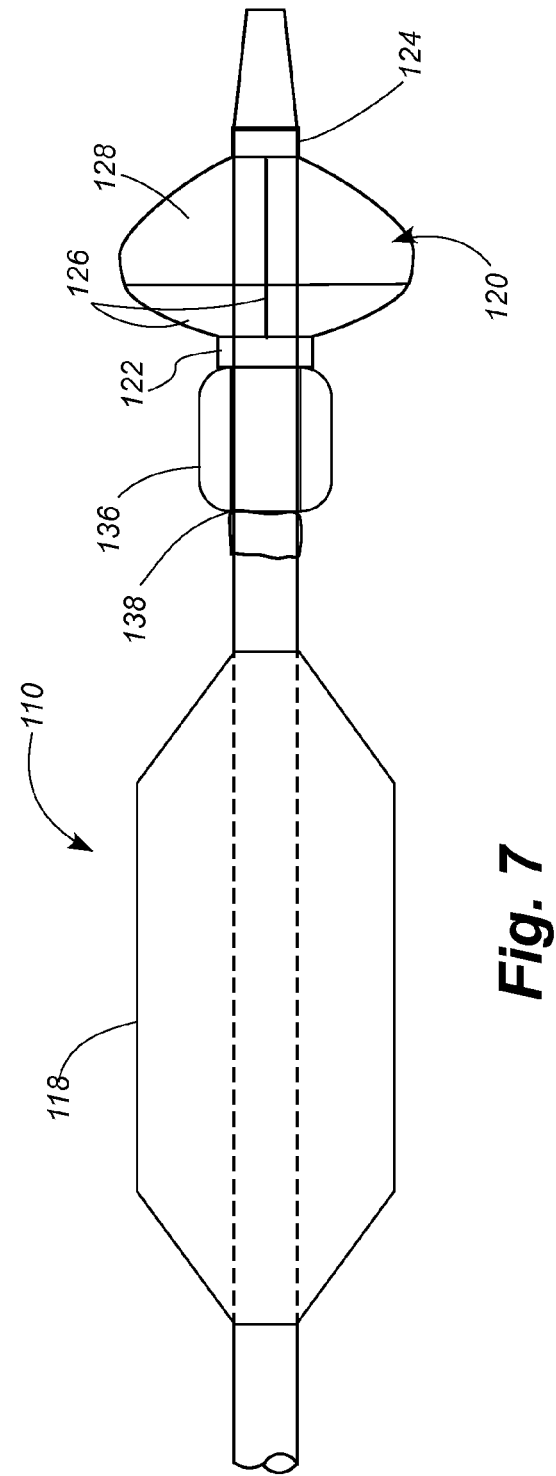

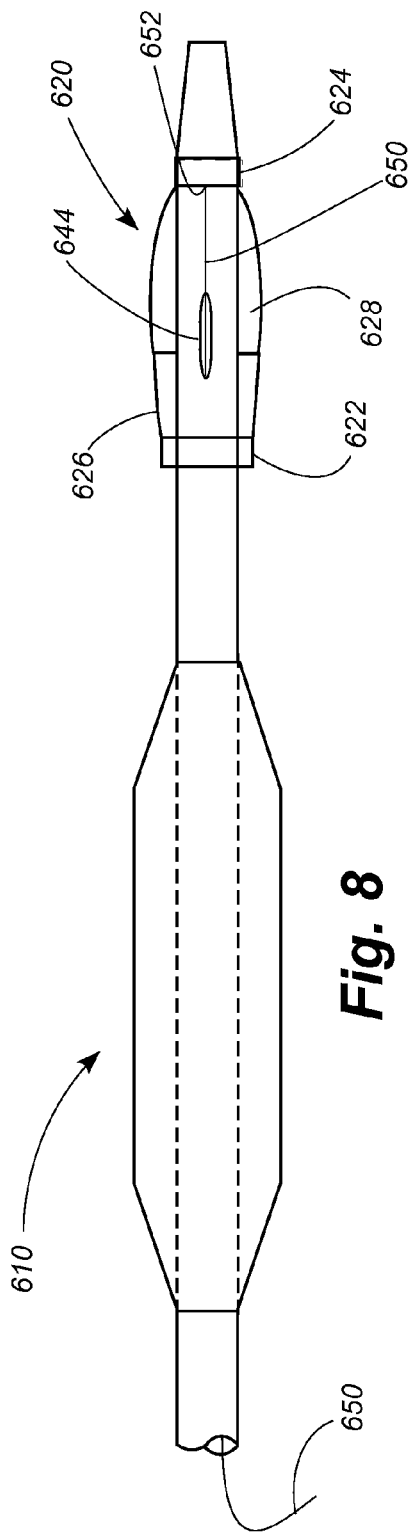
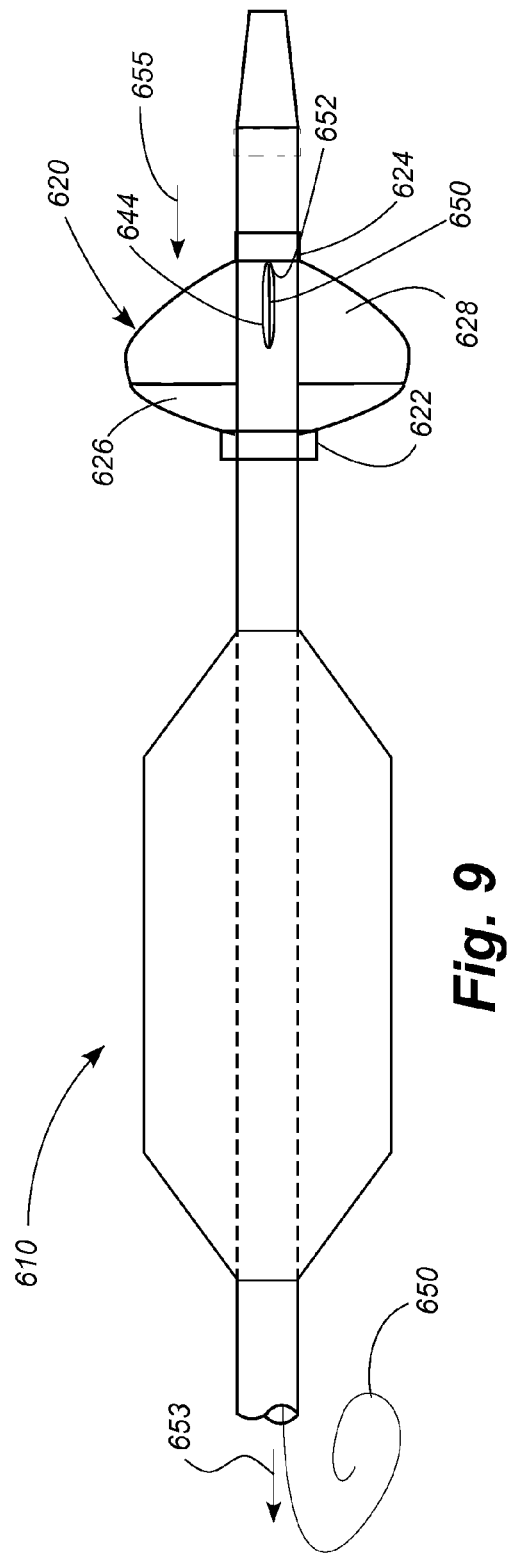

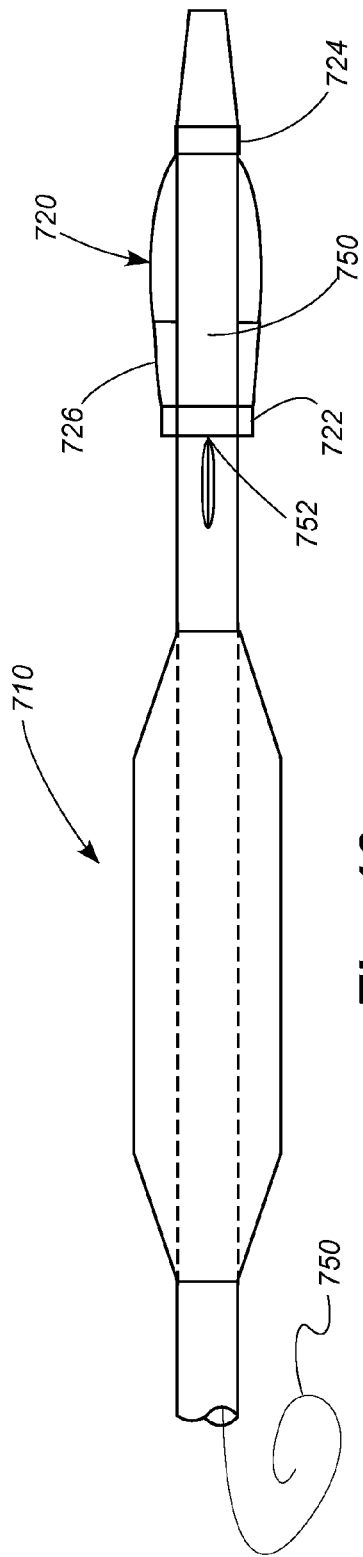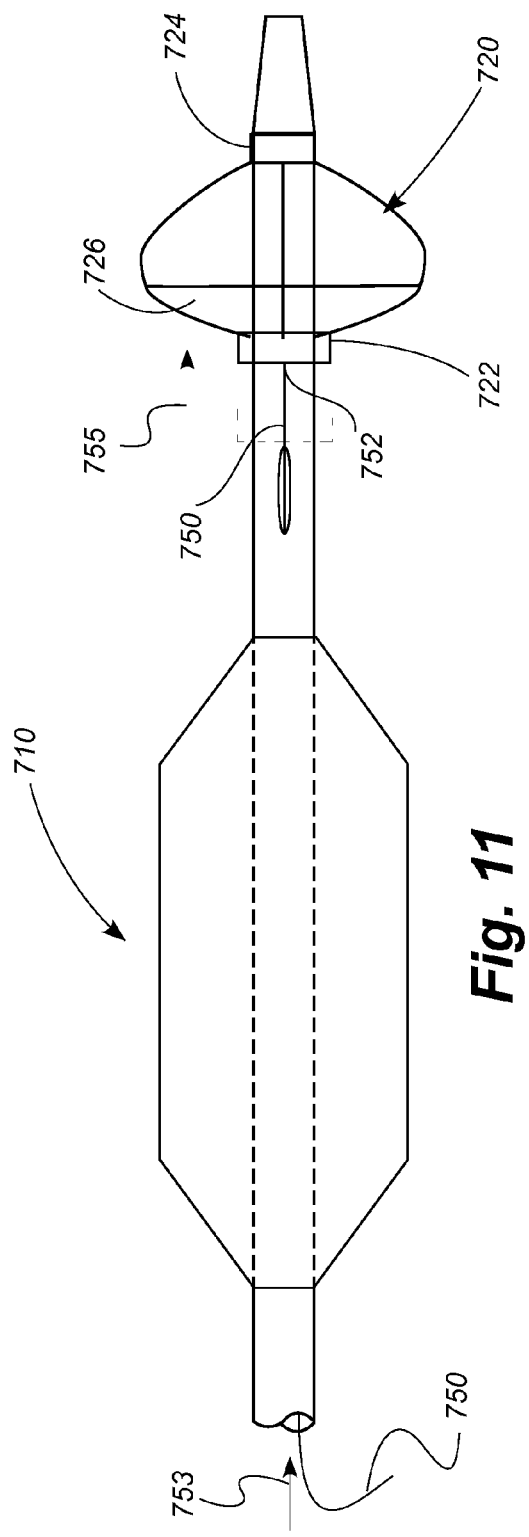

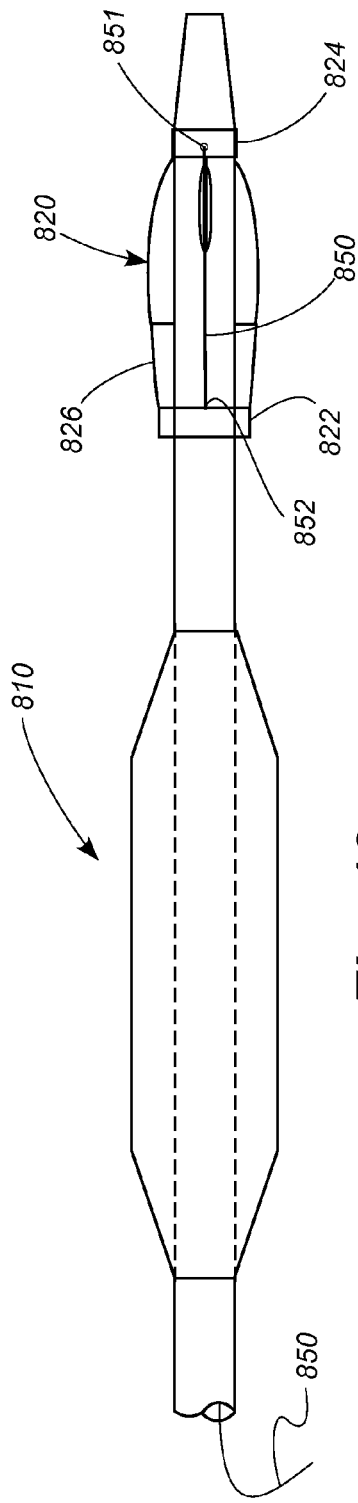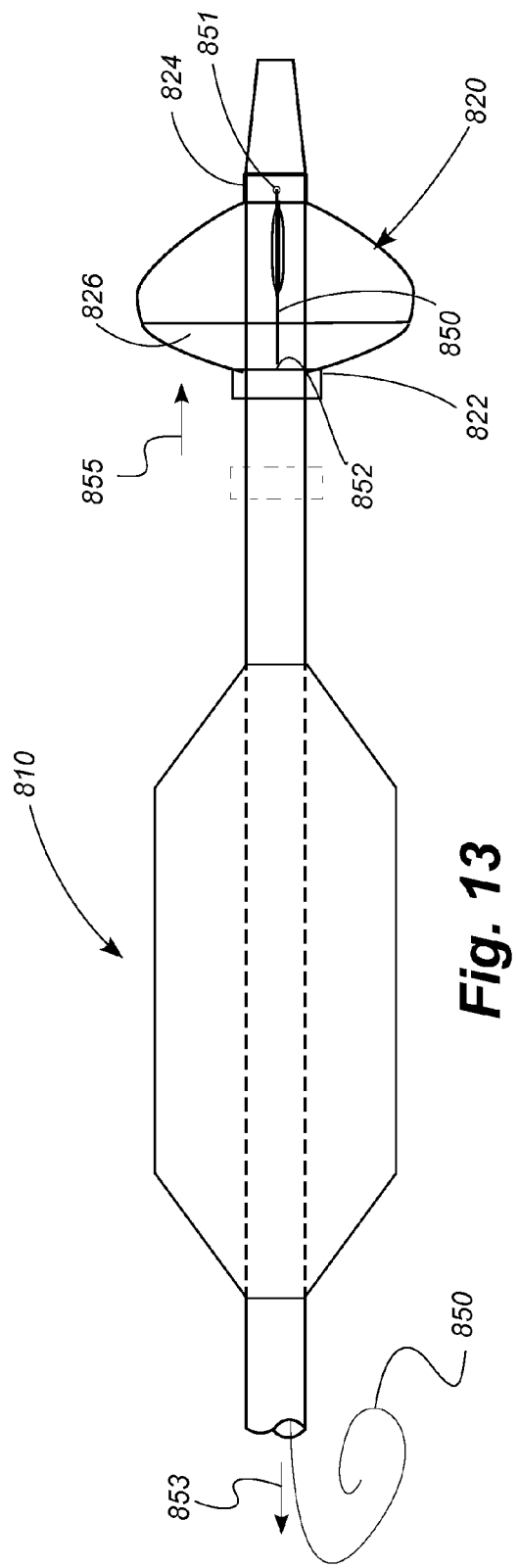

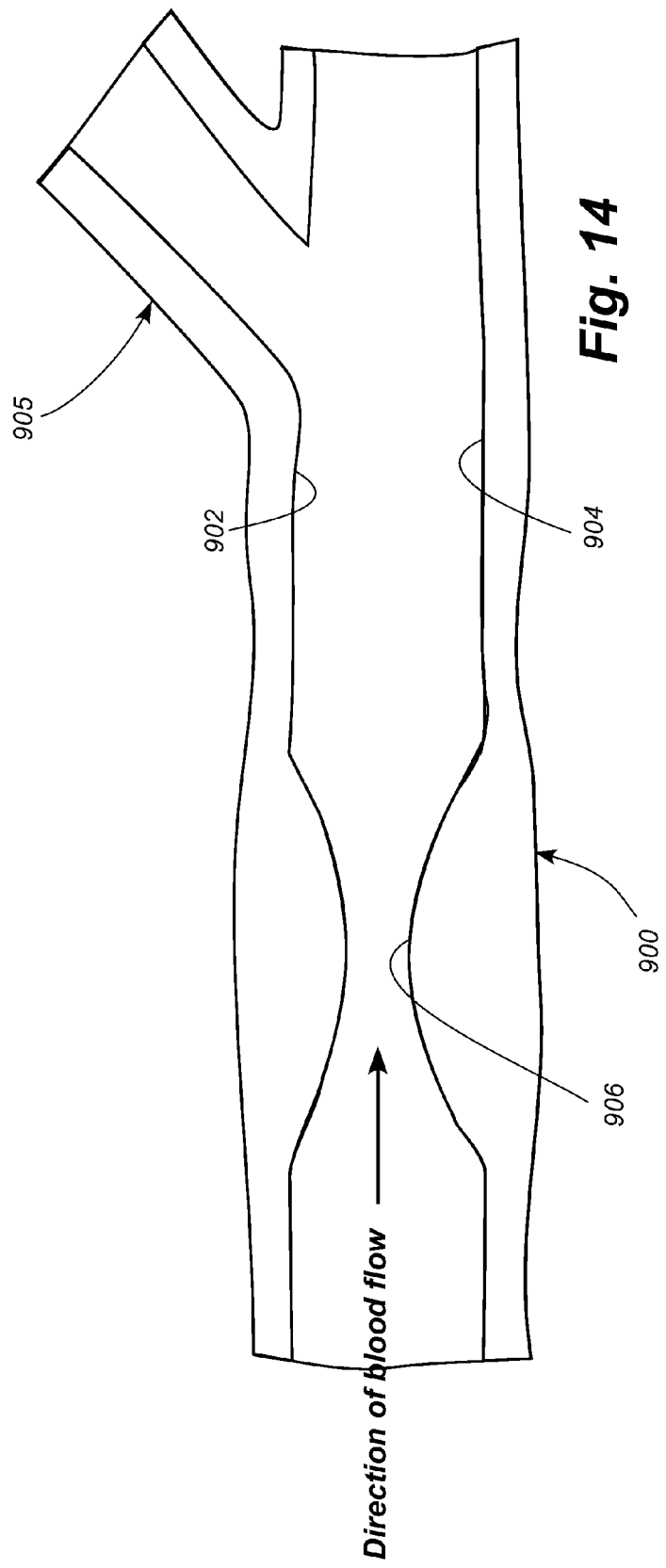

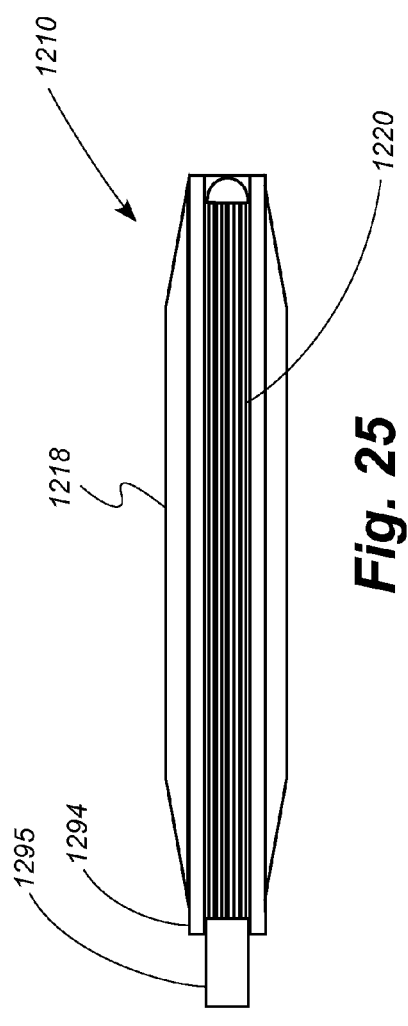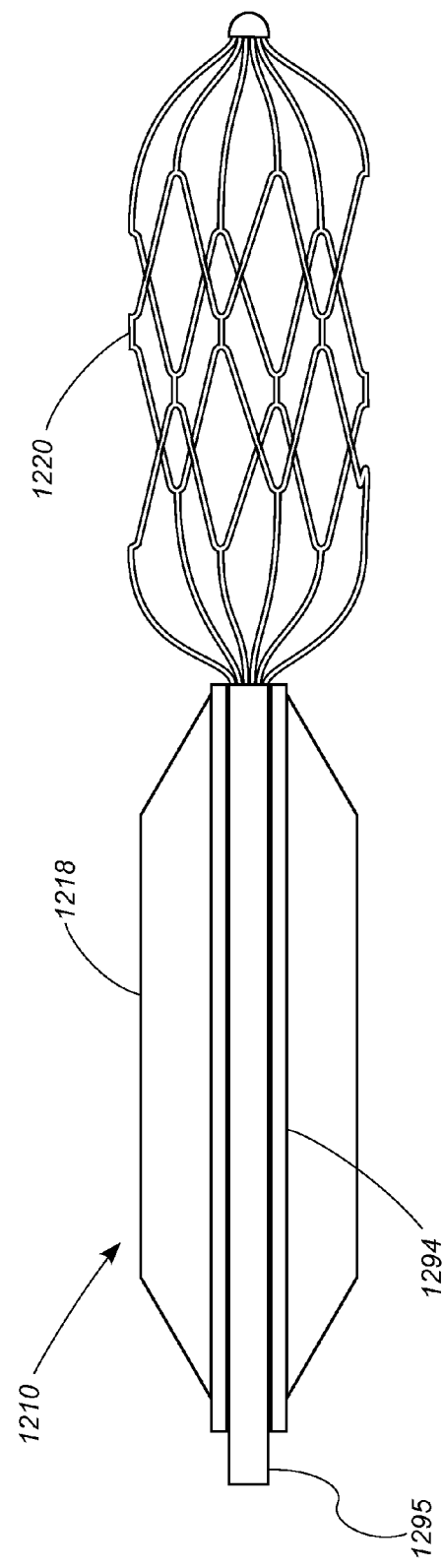

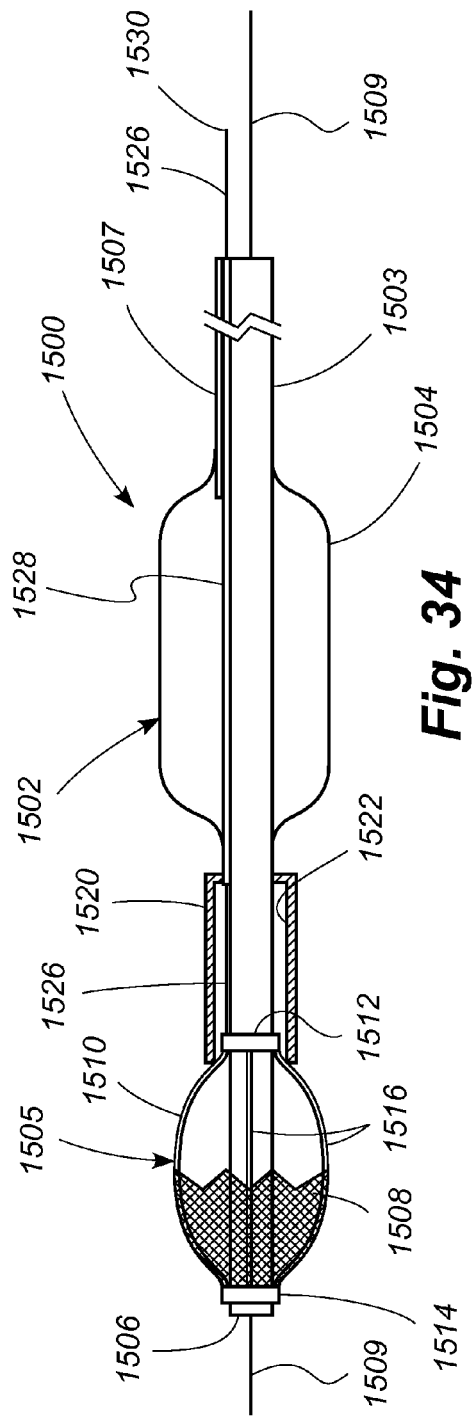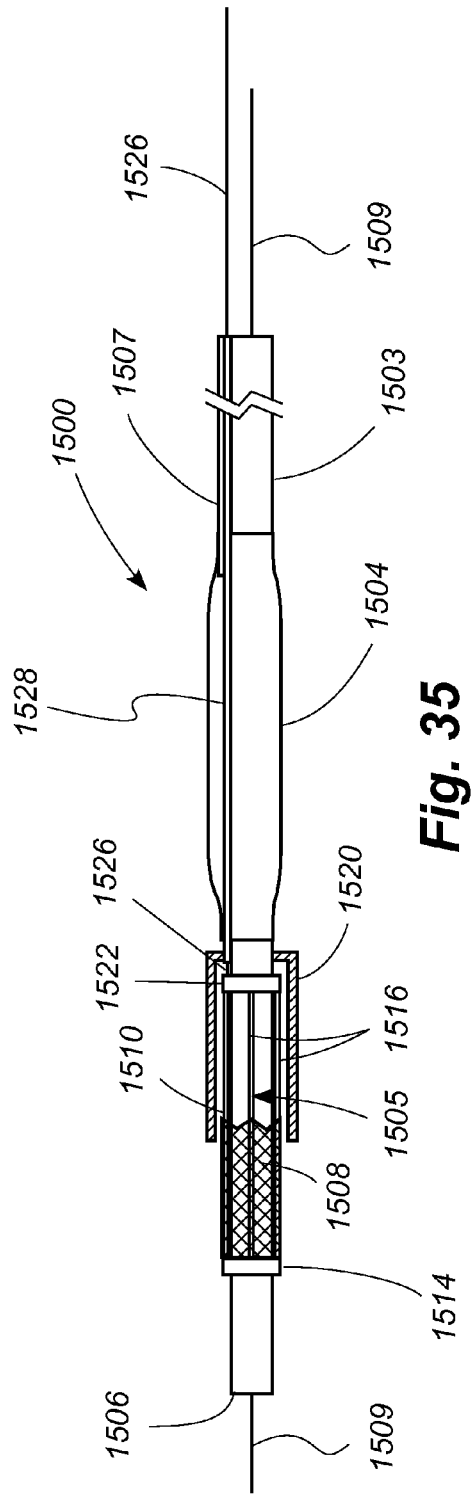

ANGIOPLASTY DEVICE WITH EMBOLIC FILTER

CROSS-REFERENCE TO RELATED APPLICATIONS

This application claims priority of U.S. Provisional Patent Application No. 61/107,391, filed Oct. 22, 2008; U.S. Provisional Patent Application No. 61/107,395, filed Oct. 22, 2008; and U.S. Provisional Patent Application No. 61/107,404, filed Oct. 22, 2008.

TECHNICAL FIELD

The present invention relates generally to surgical devices and relates more specifically to a percutaneous transluminal angioplasty device.

BACKGROUND OF THE INVENTION

The vascular bed supplies a constant flow of oxygen-rich blood to the organs. If plaque builds up in these vessels, blockages can develop, reducing blood flow to the organs and causing adverse clinical symptoms, up to and including fatality.

Angioplasty is a catheter-based procedure performed by a physician to open up a blocked vessel and restore blood flow. An entry site is opened, for example in the patient's groin, arm, or hand, and a guide wire and catheter are advanced under fluoroscopic guidance to the location of the blockage. A catheter having a small balloon adjacent its distal end is advanced under fluoroscopic guidance until the balloon lies within the stenosed region. The balloon is then inflated and deflated one or more times to expand the stenosed region of the artery.

Since diseased vessels are comprised of a range of material from early-stage thrombosis to late-stage calcified plaque, angioplasty can release embolic particles downstream from the 15 stenosed location. These embolic particles can result in adverse clinical consequences. It has been shown that it is beneficial to trap these embolic particles to prevent them from traveling downstream with blood flow to the capillary bed (e.g., Bairn D S, Wahr D, George B, et al., *Randomized Trial Of A Distal Embolic Protection Device During Percutaneous Intervention Of Saphenous Vein Aorto-Coronary Bypass Grafts*, Circulation 2002; 105: 1285-90).

In addition to balloon angioplasty, stenoses may also be treated with stents and with mechanical thrombectomy devices. These devices are also prone to releasing embolic particles downstream from the stenosed location.

There are systems available today that are used to catch these embolic particles. They are primarily filter systems or occlusion balloon systems built on a guidewire. These systems have shortcomings related to simplicity of use and crossing tight lesions with a filter or balloon guidewire that is larger in diameter than the 10 guidewire which is normally used. These embolic protection guidewires also have flexibility and stability problems that make the protected angioplasty procedure difficult in many cases. In the case of saphenous vein grafts, the problems relate specifically to aorto-ostial lesions, where the guidewire may not be long enough to provide support, or distal vein graft lesions, where there is not enough of a landing zone for the filter. The latter is a problem as currently available filter systems have a considerable distance between the treatment balloon and the distal filter. This distance is a problem not only in distal vein graft lesions, but also in arterial stenoses in which 20 there is a side branch immediately after the stenosis. In such cases, the filter can often be deployed only distal to the side branch, thus leaving the side branch unprotected from embolic particles.

BRIEF DESCRIPTION OF THE DRAWINGS

FIG. 6 is a second embodiment of a percutaneous transluminal angioplasty device.

FIG. 7 is a view of the percutaneous transluminal angioplasty device of FIG. 6 showing the angioplasty balloon inflated and the embolic filter expanded.

FIG. 8 is still another embodiment of a percutaneous transluminal angioplasty device.

FIG. 9 shows the embodiment of FIG. 8 with the angioplasty balloon inflated and the embolic filter expanded.

FIG. 10 is another embodiment of a percutaneous transluminal angioplasty device, showing an angioplasty balloon and embolic filter in their collapsed conditions.

FIG. 11 shows the embodiment of FIG. 10 with the angioplasty balloon inflated and the embolic filter expanded.

FIG. 12 is yet another embodiment of a percutaneous transluminal angioplasty device, showing the angioplasty balloon and the embolic filter in their collapsed conditions.

FIG. 13 is another view of the embodiment of FIG. 12, showing the angioplasty balloon inflated and the embolic filter expanded.

FIG. 14 shows a side cut away view of a coronary artery with a stenosis.

FIG. 25 is a side cutaway view of another embodiment of an angioplasty device showing an angioplasty balloon in its deflated condition and an embolic filter in a retracted state.

FIG. 26 is a side cutaway view of the angioplasty device of FIG. 25 showing the angioplasty balloon inflated and the embolic filter expanded.

FIG. 34 is a partially cutaway side view of another embodiment of an angioplasty device with angioplasty balloon and filter basket expanded.

FIG. 35 is a side view of the filter basket of FIG. 34 with the angioplasty balloon and filter basket collapsed.

DETAILED DESCRIPTION OF THE DISCLOSED EMBODIMENTS

Figure 1:
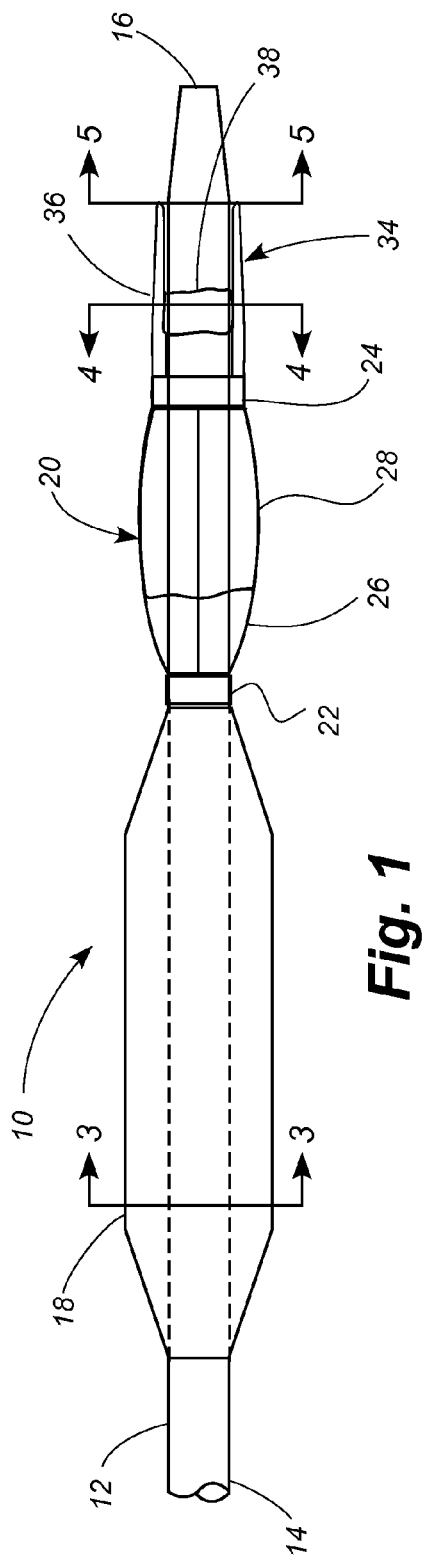
FIG. 1 is a partial cut away side view of first embodiment of a percutaneous transluminal angioplasty device according to a first disclosed embodiment, with the angioplasty balloon and embolism filter in their collapsed positions.
Figure 2:
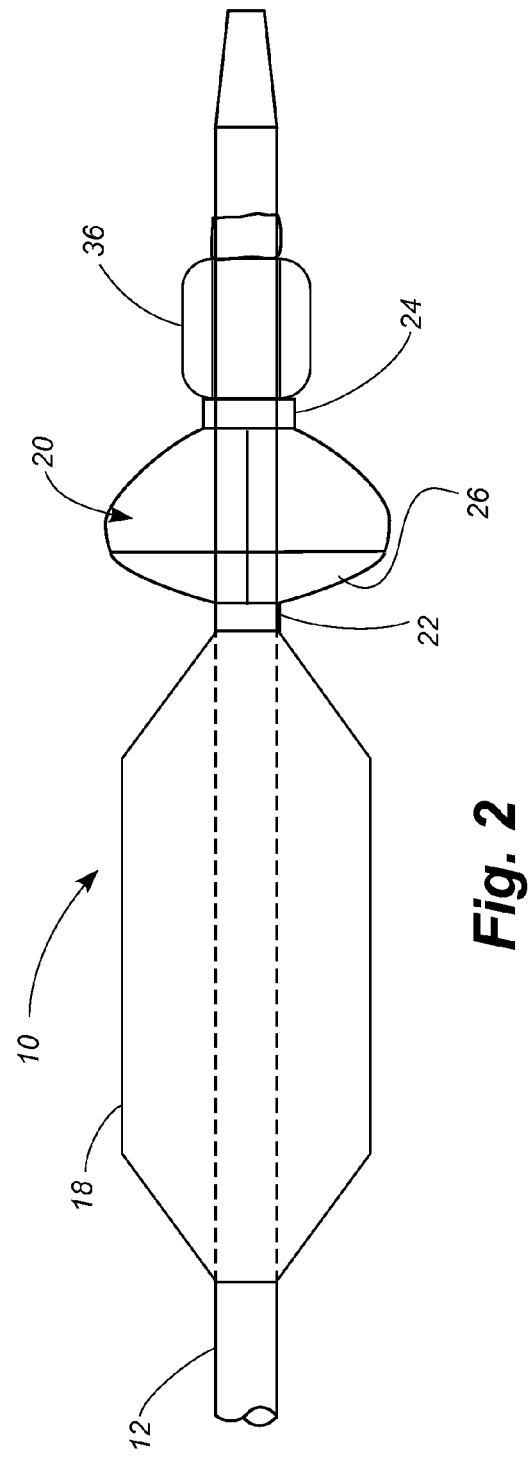
FIG. 2 is a partial cut away side view of the percutaneous transluminal angioplasty device of FIG. 1 showing the angioplasty balloon and embolism filter in their expanded positions.

Referring now to the drawings, in which identical numbers indicate identical elements throughout the various views, FIGS. 1 and 2 illustrate a first embodiment of a percutaneous transluminal angioplasty device 10. The device 10 comprises an elongated catheter 12 having a shaft 14 with a proximal end (not shown) and a distal end 16. Spaced a short distance proximally from the distal end 16 of the catheter 12 is an angioplasty balloon 18 of conventional design. In FIG. 1 the angioplasty balloon 18 is shown in a deflated or collapsed condition. In FIG. 2 the angioplasty balloon 18 is shown in an inflated condition.

Located between the angioplasty balloon 18 and the distal tip 14 of the catheter 12 is a collapsible filter 20. The filter 20 includes a proximal ring portion 22 and a distal ring portion 24. A plurality of elongated ribs 26 extend generally longitudinally between the proximal and distal rings 22, 24. These ribs can be made of a shape memory material, such as nitinol, and in their baseline position, these ribs are collapsed. A filter mesh 28 overlies the distal portion of the ribs 26. In the embodiment of FIGS. 1 and 2, the distal ring 24 is movable toward and away from the proximal ring 22. As the distal ring 24 moves toward the proximal ring 22, the ribs 26 bow outward. As the ribs 26 bow outward, the filter mesh 28 overlaying the ribs is expanded. FIG. 1 shows the filter 20 in its collapsed condition, while FIG. 2 shows the filter in its expanded condition. Means 34 are included for expanding and collapsing the filter 20 of the device 10 shown in FIGS. 1 and 2. Specifically a balloon 36 has its distal end 38 bonded to the shaft 14 of the catheter 12. When the distal ring 24 is in its withdrawn position, as shown in FIG. 1, the bulk of the balloon 36 is folded forward over the shaft 14 10 of the catheter 12. When the balloon 36 is inflated, as shown in FIG. 2, the balloon 36 expands proximally, pushing the distal ring 24 in a proximal direction, causing the ribs 26 to bow outward and thereby expanding the filter 20. When the balloon 32 is deflated, the shape memory ribs straighten, urging the distal ring 24 in a distal direction 15 and collapsing the filter 20 close to the shaft 14 of the catheter 12.

Figure 3:
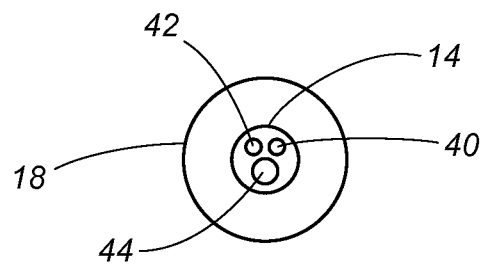
FIG. 3 is a cross sectional view taken along line 3-3 of FIG. 1.
Figure 4:
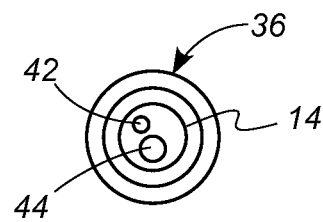
FIG. 4 is a cross sectional view taken along line 4-4 of FIG. 1.
Figure 5:
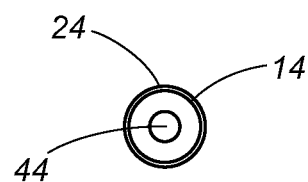
FIG. 5 is a cross sectional view taken along line 5-5 of FIG. 1.

FIGS. 3, 4, and 5 show cross sections of the device 10 at various locations along its length. Referring first to FIG. 3, the catheter shaft 12 has three lumens: two smaller lumens and a large main lumen. The two smaller lumens are inflation lumens, one lumen 40 for the angioplasty balloon 18, and one lumen 42 for the balloon 36 which controls the filter 20. The larger main lumen 44 is used to receive a guide wire (not shown) over which the device 10 advanced to position the device for performing an angioplasty procedure.

Referring now to FIG. 4, this cross section is taken at a location distal to the angioplasty balloon 18. Consequently, the angioplasty balloon inflation lumen 40 has terminated and is no longer visible. Thus, FIG. 4 shows only two lumens, the main lumen 44 for receiving the guide wire, and the smaller inflation lumen 42 for the filter balloon 36.

Referring now to FIG. 5, this cross section is taken at a location distal to the filter balloon 36, and hence only the main lumen 44 is visible.

FIGS. 6 and 7 show an alternate embodiment of a percutaneous transluminal angioplasty device 110. This device is similar to the device 10 previously described, with the exception that the filter 120, in this case, has its distal ring 124 fixed, and the proximal ring 122 of the filter 120 is movable toward and away from the distal ring to cause the ribs 126 to bow outwardly or to straighten. The balloon 136 is located on the proximal side of the filter 120 and pushes the proximal ring 122 in a distal direction when the balloon 136 is inflated.

The embodiment 610 shown in FIGS. 8 and 9 employs a different means for expanding the filter 620. In the embodiment 610 a pull wire 650 is used. The pull wire 650 extends through what would formerly have been used as the filter balloon inflation lumen 644, and the distal end 652 of the pull wire 650 is attached to the distal ring 624. When the physician wishes to raise the filter 620, he exerts a tension on the wire 650, as indicated by the arrow 653, thus drawing the distal ring 624 in a proximal direction as indicated by the arrow 655 toward the proximal ring 622. The ribs bow 626 outward, expanding the filter mesh 628 as shown in FIG. 9.

In the device 710 shown in FIGS. 10 and 11, the distal end 752 of a push wire 750 is attached to the proximal ring 722. Thus when the wire 750 is pushed in the direction indicated by the arrow 753, the proximal ring 722 is advanced distally toward the distal ring 724 in the direction indicated by the arrow 755, causing the ribs 726 to bow outward and thereby expanding the filter 720, as shown in FIG. 11.

The device 810 shown in FIGS. 12 and 13 uses a pull wire 850 to expand the filter 820. The pull wire 850 wraps around an opening 851 in the stationary distal ring 824 and extends rearward toward the proximal ring 822 to which the distal end 852 of the pull wire is attached. Thus when tension is exerted on the pull wire 850 in the direction indicated by the arrow 853, the proximal ring 822 is drawn distally toward the distal ring 824 in the direction indicated by the arrow 855, causing the ribs 826 to bow outward and thereby expanding the filter 820, as shown in FIG. 13.

The operation of the device 10 will now be explained with respect to FIGS. 14-17, and it will be understood that the other devices operate on substantially the same principles. FIG. 14 shows a vascular structure (e.g., coronary artery, saphenous vein graft, renal artery, carotid artery, superficial femoral artery, etc.) 900 with upper and lower walls 902, 904, a branch vessel 905, and a stenosis or blockage 906 caused by the build up of plaque or other substances on the arterial walls in such a way as to narrow the diameter of the arterial lumen, and in the process, constrict the flow of blood therethrough.

Figure 15:
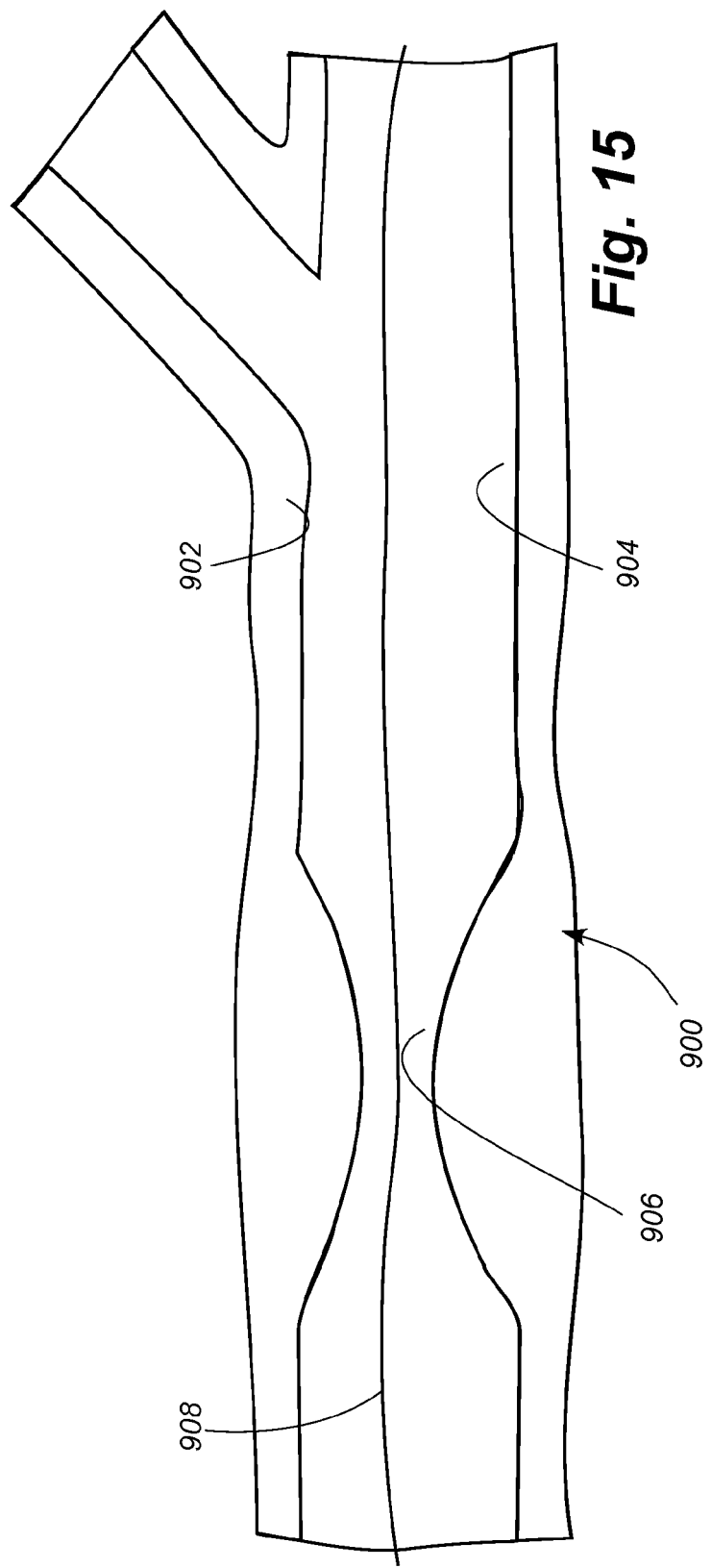
FIG. 15 shows the coronary artery of FIG. 12 with a guide wire fed through the coronary artery and through the stenosis.

In FIG. 15, a guide wire 908 has been inserted by the physician, such as through the femoral artery, and guided through the vascular system until the guide wire passes through the stenosis 906 in the vascular structure 900.

Figure 16:
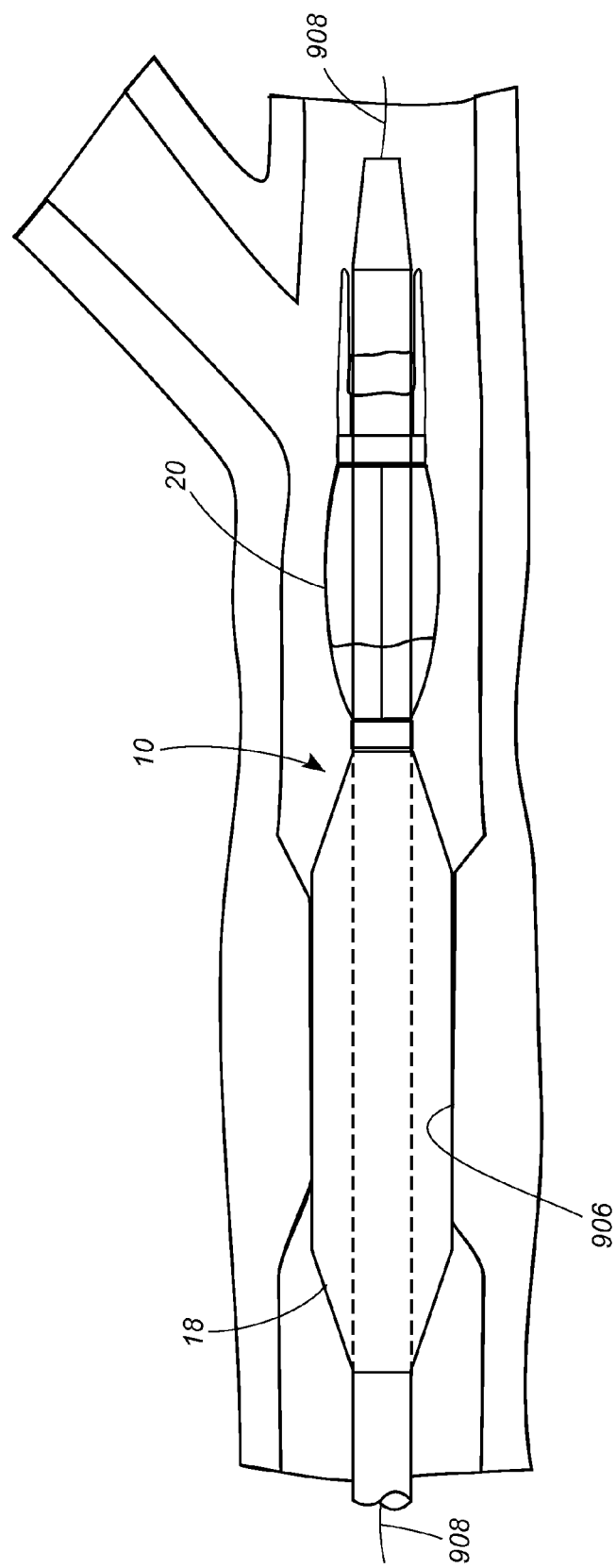
FIG. 16 shows the device of FIG. 1 threaded over the guide wire of FIG. 15 and positioned such that the angioplasty balloon is located within the stenosis.

Referring now to FIG. 16, the apparatus 10 has been inserted over the guide wire 908 and advanced to a location wherein the angioplasty balloon resides within the stenosis 906. The embolic filter 20 resides a few centimeters distal or downstream from the angioplasty location. In FIG. 16 both the angioplasty balloon and the embolic filter are shown in their collapsed conditions.

Figure 17:
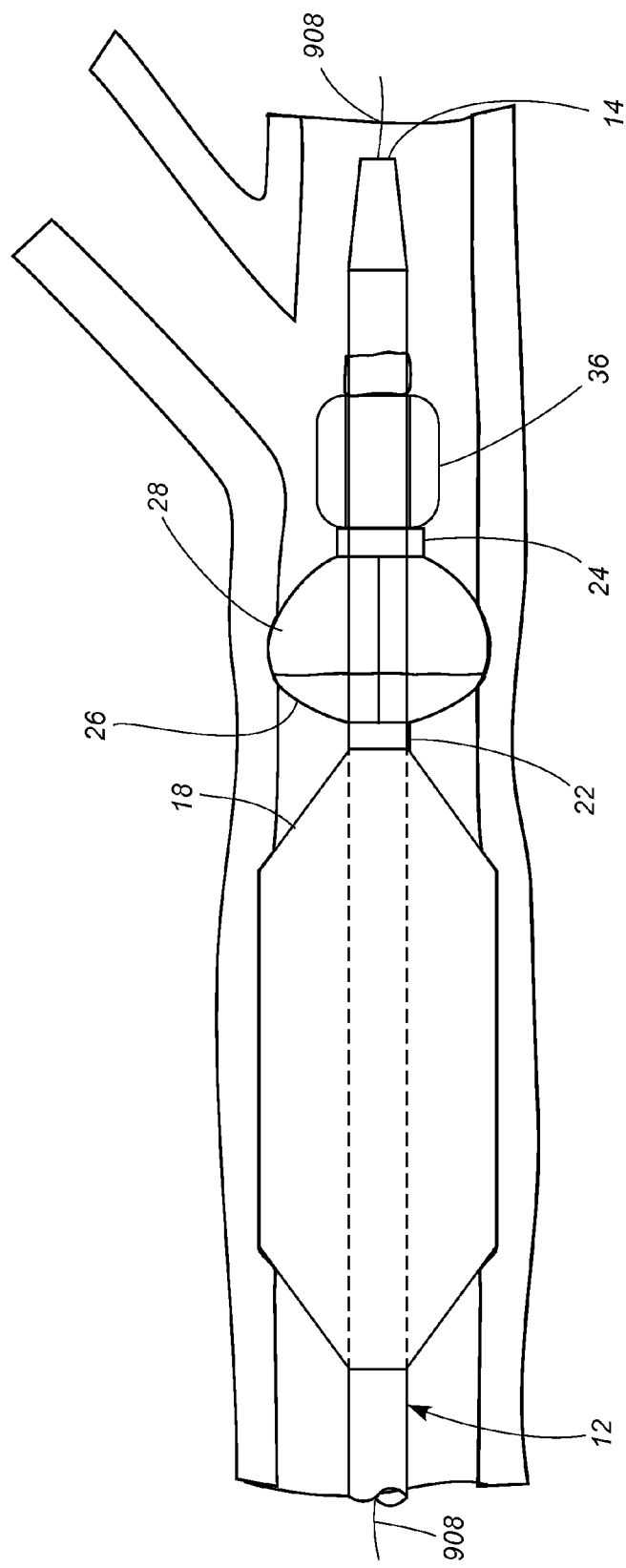
FIG. 17 illustrates the angioplasty balloon in its inflated condition to reduce the stenosis; the embolic filter has been expanded to capture any embolic particles that may break loose into the blood stream as a result of the angioplasty procedure.

In FIG. 17 the embolic filter 20 has been expanded by inflating the filter balloon 36, causing the distal ring 22 to slide in a proximal direction along the catheter shaft 12. As the ribs 26 bow outward, the mesh filter material 28 supported by the ribs spreads so as to cover substantially the entire arterial lumen. The angioplasty balloon 18 is now inflated. As the balloon 1 S inflates, it pushes tissue and plaque forming the stenosis 906 outward, opening the stenosis and possibly loosening embolic particles in the process. Any such embolic particles which get captured in the blood stream will be caught by the embolic filter 20 and will thereby be prevented from traveling to a location where they can cause clinical damage.

Of interest in FIG. 17 is the close proximity in which the filter 20 is expanded relative to the stenosis 906. Despite the short "landing area" between the stenosis 906 and the branch vessel 905, the filter 20 is expanded to capture embolic particles upstream of the branch vessel.

When removing the device 10 from the coronary artery, the preferred procedure is to deflate the angioplasty balloon 18 first, prior to collapsing the embolic filter 20. In this way, any embolic particles that are broken loose as the angioplasty balloon 18 deflates will be captured by the filter 20. The embolic filter balloon 20 is then deflated, permitting the ribs 26 and filter mesh 28 to collapse against the shaft 14 of the catheter 12. Any embolic particles captured by the mesh 28 are trapped against the shaft 14. The device 10 is then withdrawn over the guide wire 908 and removed from the patient's body.

Figure 18:
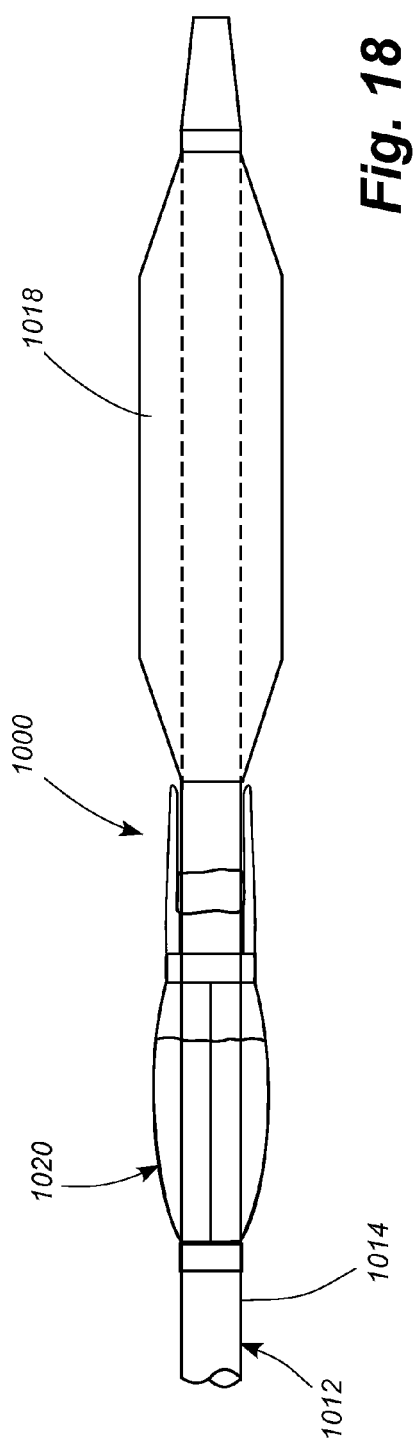
FIG. 18 is a partial cut away side view of an embodiment of a device in which the angioplasty balloon and embolism filter, shown in their collapsed positions, are reversed on the catheter shaft for peripheral vascular applications in which blood flows in the opposite direction.
Figure 19:
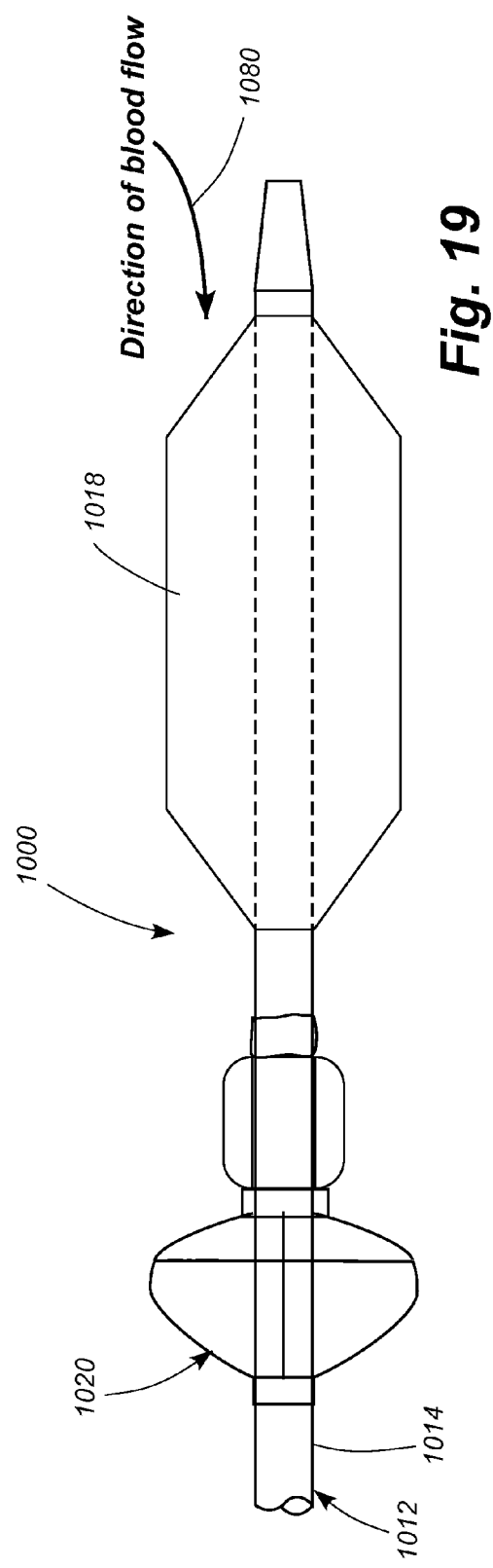
FIG. 19 is a partial cut away side view of the device of FIG. 18 showing the angioplasty balloon and embolism filter in their expanded positions.

In various peripheral vascular applications, it may be necessary to insert the catheter against the direction of blood flow (e.g., the aorta). FIGS. 18 and 19 illustrate a device 1000 in which the angioplasty balloon 1018 and the embolic filter 1020 are reversed on the shaft 1014 of the catheter 1012. Thus with the blood flowing within the vessel in the direction indicated by the arrow 1080, the embolic filter 1020 will be proximal to the angioplasty balloon 1018 and thus positioned to capture any embolic particles that may be dislodged by the angioplasty balloon. While the embodiment 1000 of FIGS. 18 and 19 employs the same method and device for expanding the embolic filter as the embodiment 10 of FIGS. 1-3, it will be understood that the methods and devices for expanding the embolic filter of other embodiments disclosed above are equally applicable to a configuration like the device of embodiment 1000 where the angioplasty balloon is positioned between the embolic filter and the tip of the device.

Figure 20:
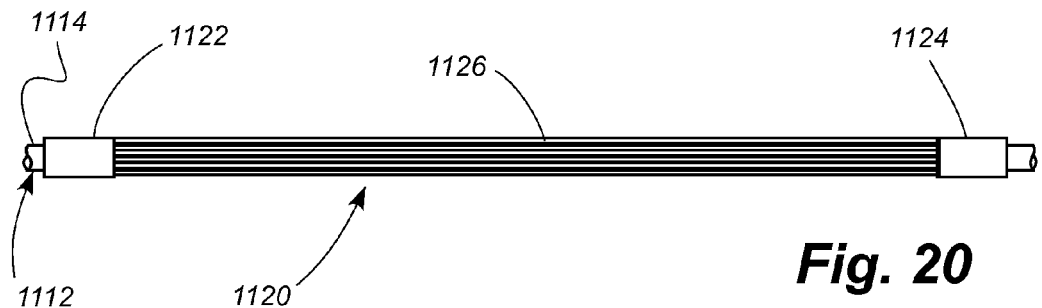
FIG. 20 is a side view of an embolism filter according to another embodiment.
Figure 21:
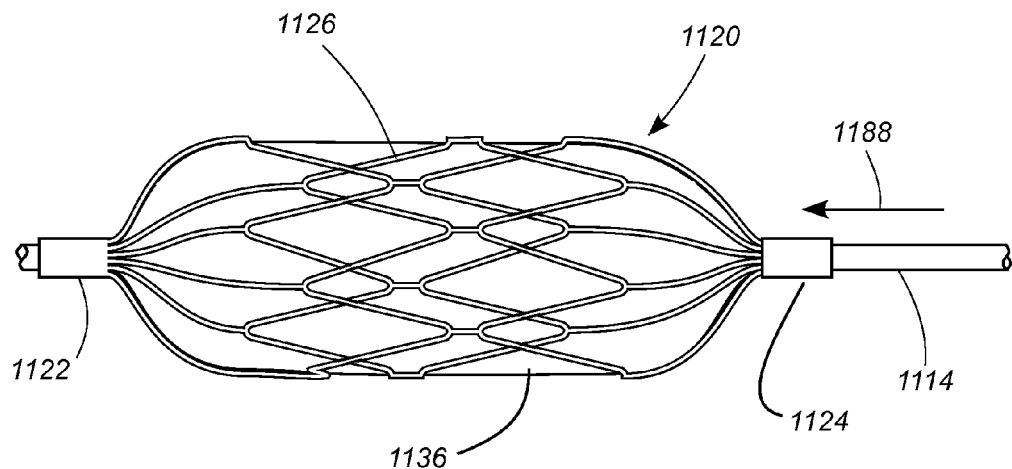
FIG. 21 is a side view of the embolism filter of FIG. 20 with the inflation balloon expanded to expand the embolism filter; filter mesh is shown removed to reveal interior detail.
Figure 22:
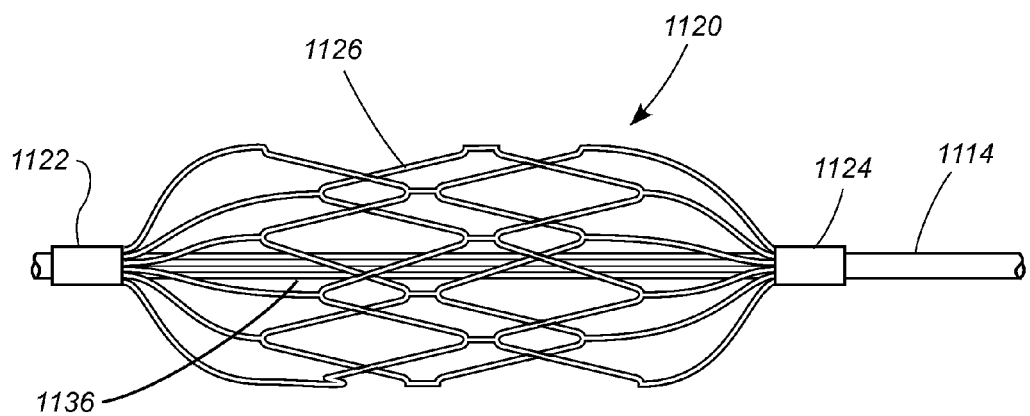
FIG. 22 is a side view of the embolism filter of FIG. 20 with the inflation balloon deflated; filter mesh is shown removed to reveal interior detail.
Figure 23:
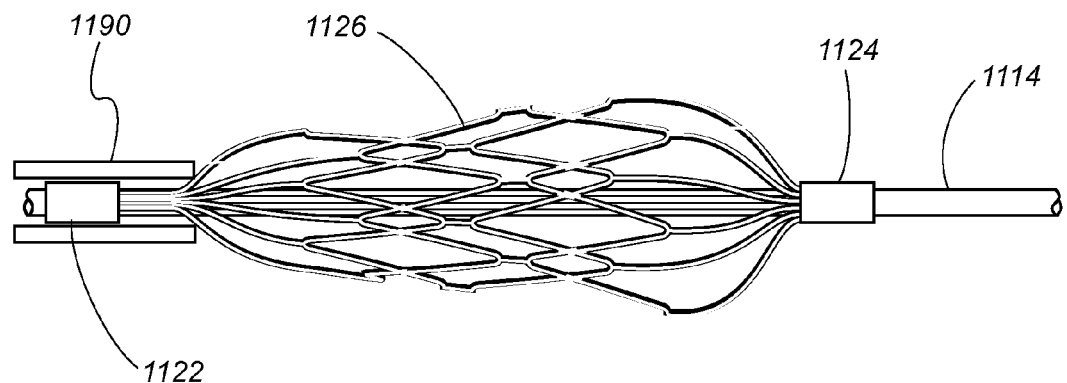
FIG. 23 is a side view of the embolism filter of FIG. 20 being retracted into the forward end of a catheter to collapse the filter; filter mesh is shown removed to reveal interior detail.

FIGS. 20-24 show still another embodiment of an embolic filter 1120 for use in conjunction with an angioplasty balloon. FIGS. 20-24 show only the embolic filter 1120 and not the angioplasty balloon, but it will be understood that the embolic filter is located on the same catheter 1114 as the angioplasty balloon in the same manner as the embodiments previously disclosed. Further, FIGS. 21-23 show the embolic filter 1120 without its filter mesh 1128 for clarity of illustration.

In FIG. 20 the embolic filter 1120 is folded closely against the shaft 1114 of the catheter 1112. The ribs 1126 of the filter 1120 extend between a proximal ring portion 1122 and a distal ring portion 1124. The distal ring portion 1124 is slidably mounted on the shaft 1114 of the catheter 1112, and the proximal ring portion 1122 is fixed with relation to the shaft of the catheter. In FIG. 21 the embolic filter balloon 1136 has been inflated, expanding the ribs 1126 of the embolic filter. As the ribs expand, the distal ring portion 1124 slides in the proximal direction, as shown by the arrow 1188. Once expanded, the ribs 1126 maintain their shape, such that when the embolic filter balloon 1136 is deflated, as shown in FIG. 22, the embolic filter 1120 remains expanded.

To retract the embolic filter 1120, a second, outer catheter 1190 is advanced over the catheter 1112, as shown in FIG.

23, causing the ribs 1126 to collapse as the embolic filter is withdrawn into the forward end of the outer catheter 1190. As the ribs 1126 collapse, the distal ring portion 1124 slides in the distal direction. Once the embolic filter 1120 has been completely retracted into the forward end of the outer catheter 1190, the outer and inner catheters are withdrawn simultaneously.

Figure 24:
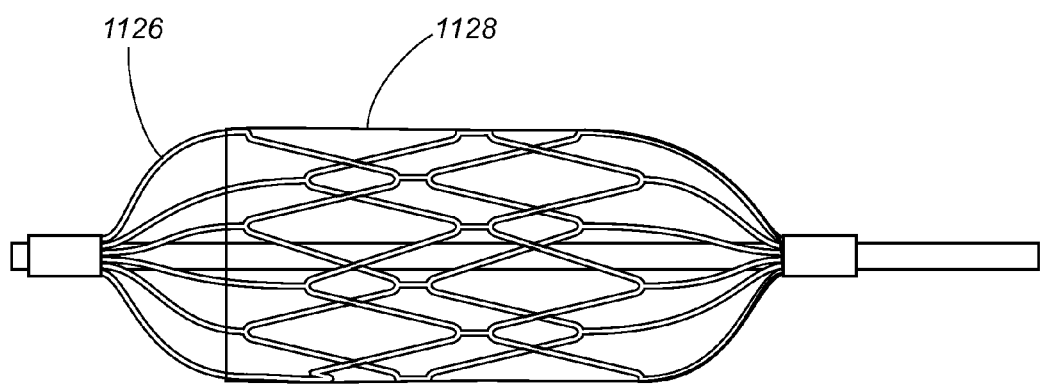
FIG. 24 is a side view of the embolism filter of FIG. 20 with the filter expanded and filter mesh in place.

FIG. 24 shows the embolic filter 1120 with filter mesh 1128 positioned over the ribs 1126.

FIGS. 25 and 26 illustrate a further embodiment of a percutaneous angioplasty device 1210, in which the embolic filter 1220 is located on a different carrier than the angioplasty balloon 1218. Specifically, the angioplasty balloon 1218 is located on an outer catheter 1294, and the embolic filter 1220 is located at the forward end of an inner catheter 1295. (The embolic filter 1220 is shown without filter mesh in FIGS. 25 and 26 for clarity of illustration.) The outer catheter preferably has three lumens, one for inflating the angioplasty balloon 1218, one for accommodating a guide wire (not shown), and one for receiving the inner catheter 1295 and embolic filter 1220. The inner catheter 1295 is slidably telescopically disposed within the outer catheter 1294. The ribs 1226 of the embolic filter 1220 are formed from a shape-memory metal such as nitinol and are constructed to normally assume an "open" configuration. When retracted within the forward end of the outer catheter 1294, the ribs 1226 of the embolic filter collapse.

To use the percutaneous angioplasty device 1210, the inner catheter is inserted into the outer catheter so that the embolic filter 1220 is collapsed within the distal end of the device, as shown in FIG. 25. The outer and inner catheters 1294, 1295 are inserted together, such as through the femoral artery, over a guidewire and advanced through the vascular system to a location wherein the uninflated angioplasty balloon 1218 resides within the stenosis. Once location of the angioplasty balloon 1218 within the stenosis has been verified by suitable medical imaging technology, the inner catheter is advanced to progress the embolic filter 1220 beyond the forward end of the outer catheter 1294. As the embolic filter 1220 is freed from the confines of the outer catheter 1294, the ribs assume their expanded configuration and expand the embolic filter. Thereafter the angioplasty balloon 1218 may be inflated to treat the stenosis, and any emboli loosened during the procedure will be captured by the embolic filter 1220 downstream of the stenosis.

When the angioplasty procedure has been completed, the angioplasty balloon 1218 is deflated, and the embolic filter 1220 is withdrawn back into the forward end of the outer catheter 1294. The outer and inner catheters 1294, 1295 are then withdrawn together from the patient.

In the foregoing embodiment a wire can be substituted for the inner catheter 1295 as a means for carrying the embolic filter 1220.

Figure 27:
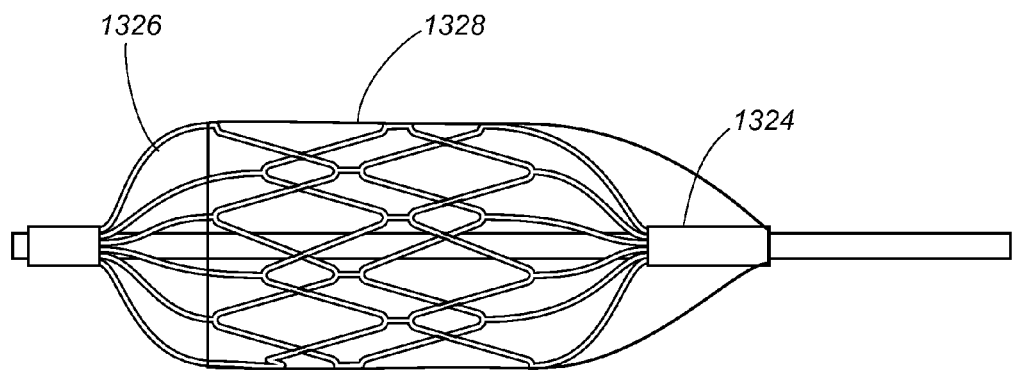
FIG. 27 is a side view of a further embodiment of an angioplasty device in which the filter mesh extends beyond the end of the ribs so as to form a sac when the filter is collapsed.
Figure 28:
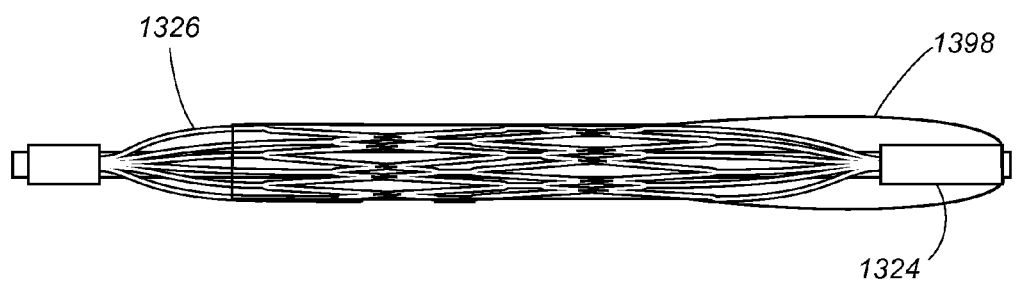
FIG. 28 is a side view of the angioplasty device of FIG. 27 showing the filter in its collapsed condition.

FIGS. 27 and 28 show an angioplasty device 1310 that is identical to the device 10, with the exception that the filter mesh 1328 extends distally beyond the end of the ribs 1326 and is attached to the distal end of the distal ring 1324. When the filter 1320 is collapsed, as shown in FIG. 28, a sac 1398 is formed which helps contain the embolic particles, thereby minimizing the possibility that the ribs 1326 will squeeze the particles out of the filter.

Figure 29:
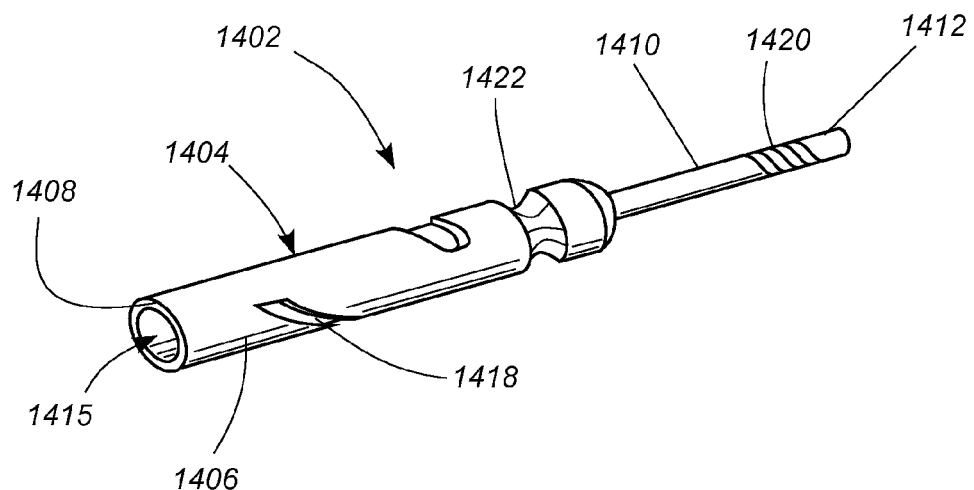
FIG. 29 is an isometric view of a pusher, which is an internal component of an actuator shown in FIG. 33.

Referring now to FIGS. 29-33, a proximal actuator 1400 (FIG. 33) is shown for actuating the pull-wire (e.g., the pull wire 650 in FIGS. 8 and 9) that manipulates the embolic filter. FIG. 29 shows a pusher 1402, one of the internal components of the actuator 1400. The pusher comprises an elongated body 1404 consisting of a larger cylindrical element 1406 at the distal end 1408, which tapers to a smaller cylindrical portion 1410 at the proximal end 1412. The larger cylindrical element 1406 of the disclosed embodiment is approximately 1.0 inches in length, has an outer diameter of approximately 0.278 inches, and an inner diameter of approximately 0.10 inches. The smaller cylindrical element 1410 is approximately 0.75 inches in length and has an outer diameter of approximately 0.180 inches. The body 1404 has a through hole 1415 that will allow the pull wire 650, also referred to as an actuation wire, to slide through easily. In the disclosed embodiment, the through hole is 0.025 inches. A spiral groove 1418 is cut into one section of the larger cylindrical portion 1406. The axial length of the spiral groove 1418 is equal to the total movement of the actuation wire 650 required to fully deploy the filter (not shown in FIGS. 29-33 for clarity of illustration). In the disclosed embodiment, the axial length of the spiral groove 1418 is 14 mm for carotid, 12 mm for renal, and 10 mm for coronary applications. The pusher 1402 of the disclosed embodiment is manufactured of Delrin™ but can be made from any other suitable rigid plastic or metal.

Figure 33:
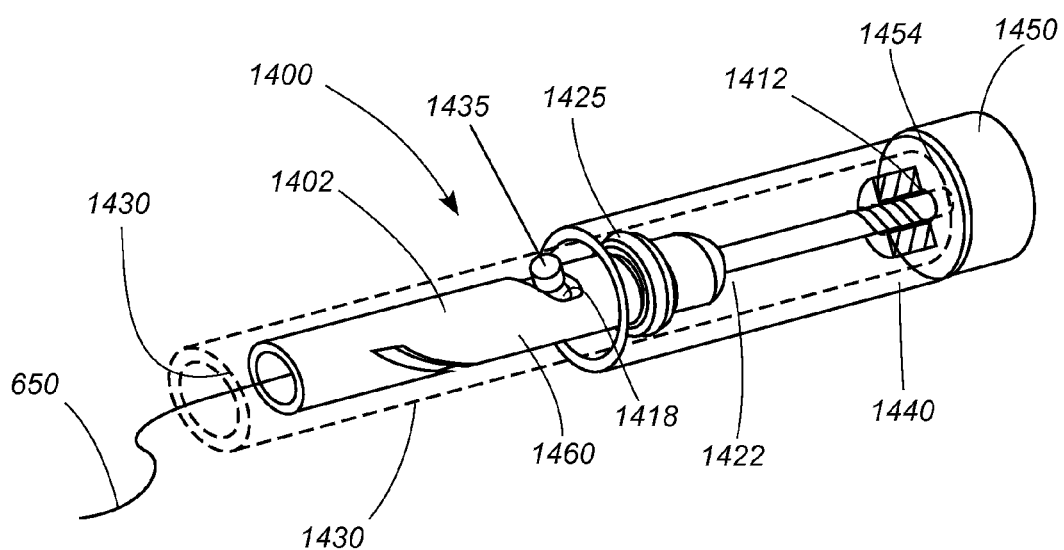
FIG. 33 is an isometric view of an actuator, with some parts shown in phantom and other parts cut away to reveal interior detail.

The proximal end 1412 of the pusher 1402 has a standard thread 1420 formed on its exterior surface. On the exterior surface of the pusher at a location between the spiral groove 1418 and the threaded portion 1420 there is radial slot 1422 to accommodate an O-ring 1425 (FIG. 33). The diameter at the base of the radial slot is approximately 0.168 inches. The O-ring has an inner diameter that fits into the slot 1422 of the pusher 1402 and an outer diameter that is slightly larger than the diameter of the pusher. The O-ring 1425 of the disclosed embodiment is made of silicon, but the O-ring can be made from any suitable resilient material.

Figure 30:
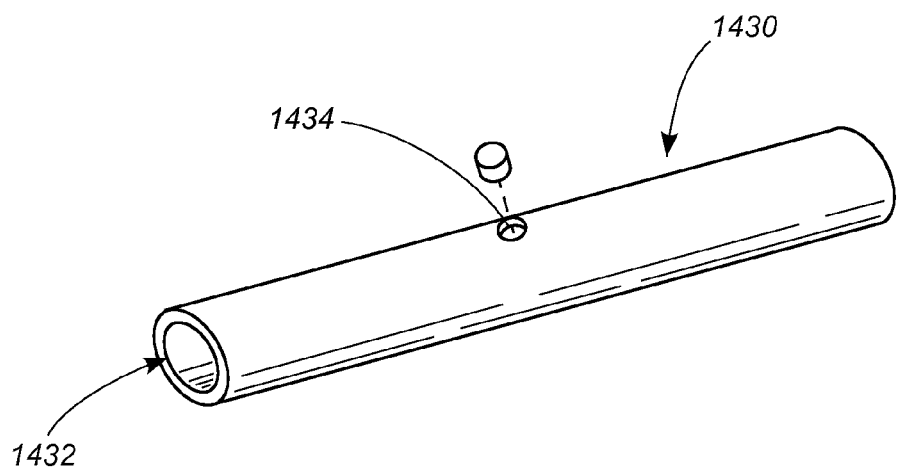
FIG. 30 is an isometric view of a housing, which is a component of the actuator shown in FIG. 33.

Referring now to FIG. 30, a tubular housing 1430 of the actuator 1400 is shown. The housing 1430 has an axial bore 1432. A radial bore 1434 is formed through one exterior wall at a location distal of the midpoint of the housing. A cylindrical dowel 1435 fits snugly into the radial bore 1434 and is held in place by an interference fit. When positioned, the dowel protrudes radially into the axial bore 1432 of the housing 1430.

Figure 31:
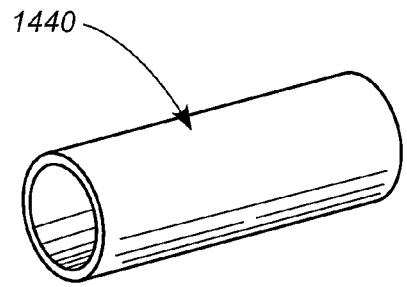
FIG. 31 is an isometric view of a skirt, which is a component of the actuator shown in FIG. 33.

The housing 1430 of the disclosed embodiment is approximately 2.5 inches long. The outer diameter of the housing 1430 is approximately 0.40 inches, and the inner diameter of the housing is approximately 0.28 inches, which is slightly larger than the exterior diameter of the pusher 1402. The dowel of the disclosed embodiment is 0.075 inches OD×0.060 inches in length. In the disclosed embodiment the dowel is made of steel or other suitable material FIG. 31 illustrates a skirt 1440 of the actuator 1400. The skirt 1440 is a tubular component that has an inner diameter of sufficient size to accommodate the housing 1430. In the disclosed embodiment, the skirt is approximately 1.0 inches in length and has an outer diameter of approximately 0.5 inches and an inner diameter of approximately 0.425 inches.

Figure 32:
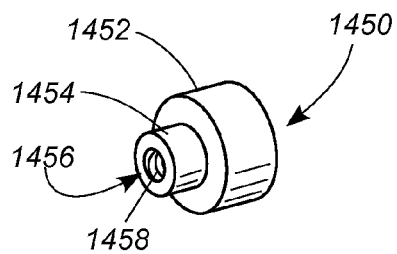
FIG. 32 is an isometric view of a knob, which is a component of the actuator shown in FIG. 33.

FIG. 32 shows a knob 1450 of the actuator 1400. The proximal portion 1452 of the knob of the disclosed embodiment is a cylinder and has an outer diameter of approximately 0.630 inches, but the knob can be configured to be of any size and shape that is convenient to be grasped by a user. The outer surface of the proximal portion 1452 is preferably knurled, grooved, roughened or otherwise provided with a suitable non-slip surface to facilitate gripping by a user. The knob has a barrel portion 1454 coaxial with and extending distally from the proximal portion 1452. The barrel portion has an outer diameter of approximately 0.420 inches. A coaxial through hole 1456, at least the distal portion of which is threaded with a standard thread 1458, is formed through the knob 1450.

Referring now to FIG. 33, the pusher 1402, O-ring 1425, housing 1430, skirt 1440, and knob 1450 are assembled to form the actuator 1400. The O-ring 1425 is positioned within the radial slot 1422 (FIG. 29) in the pusher 1402. The pusher 1402 is then positioned coaxially within the bore 1432 of the housing 1430. The exterior diameter of the O-ring 1425 is sufficiently large to create an interference fit with the inner wall of the housing 1430. This interference fit normally prevents the pusher 1402 from rotating relative to the housing 1430 in the absence of an outside force but permits the pusher 1402 to rotate within the housing 1430 when a rotational force is applied.

With the pusher 1402 in position within the housing 1430, the cylindrical dowel 1435 is pressed snugly through the radial bore 1434 in the housing 1430 so that its inner end rides within the spiral groove 1418 in the pusher.

The proximal end of the actuator wire 650 is fed through the distal end of the housing 1430 and down the through bore 1415 of the pusher 1402. As the wire 650 exits the proximal end of the pusher 1402, it is bent 180° so that it extends along the threaded proximal end 1412 of the pusher 1402. The knob 1450 is then screwed onto the threaded proximal end 1412 of the pusher 1402, capturing the proximal end of the actuator wire 650 between the knob and the pusher and anchoring it in place. The skirt 1440 is then coupled to the knob 1450 by way of an interference fit between the inner wall of the proximal end of the skirt and the outer surface of the barrel portion 1454 of the knob 1450.

To use the actuator 1400, the user grasps the knob 1450 between the thumb and forefinger. As the knob 1450 is rotated counter-clockwise, the inner end of the dowel 1460 riding in the spiral groove 1418 of the pusher 1402 causes the pusher to advance axially, extending the actuator wire 650. As the knob 1450 is rotated clockwise, the actuator wire 650 retracts.

The actuator 1400 provides several advantages. The device can be actuated with one hand. Operation of the device is also intuitive: counterclockwise rotation of the knob 1450 opens the device, clockwise rotation closes it. Also, the interference fit between the O-ring 1425 and the housing 1430 allows the physician to stop the actuation of the wire 625 at any point without having to affirmatively "lock" the device to hold the wire in place.

In addition to ease of use and convenience, the actuator 1400 enables more precise actuation of the filter. Because the axial length of the spiral groove 1418 on the pusher 1402 corresponds to the amount by which the actuator wire 650 needs to be advanced or retracted to open or close the filter, the actuator 1400 takes the "guesswork" out of the operation of the device and prevents the physician from under-extending the wire (and not fully opening the filter) and over-extending the wire (and possibly damaging the device).

FIGS. 34 and 35 disclose an angioplasty device 1500. The device 1500 includes a balloon catheter 1502 comprising a catheter shaft 1503 and a balloon 1504. The balloon 1504 is inflatable by means of an inflation lumen 1507. A filter basket 1505 is disposed at the distal end 1506 of the shaft 1503. To facilitate guidance of the device 1500 to the treatment location within the patient's body, a guidewire 1509 is received through a lumen (not shown) extending through the catheter shaft 1503.

The filter basket 1505 consists of a filter membrane 1508 attached to a support frame 1510. The support frame 1510 is generally tubular in shape with a proximal ring 1512 and a distal ring 1514 at opposite ends. A first set of elongated struts 1516 is attached to and extends between the end rings 1512, 1514. The frame 1510 of the filter basket 1504 is formed from Nitinol or other suitable shape-memory material.

For ease of illustration, the frame 1510 of the device 1500 is shown as only one set of elongated struts 1516. However, it will be appreciated that a second set of struts may be located in between the first set of longitudinal struts 1516 to form a serpentine pattern. This second set of struts is formed of strut sections connected by hinges. The width of the hinges is different than the width of the adjacent strut sections so as to provide a zone of weakness along which the hinges bend. The bending of the hinges allows the second set of serpentine struts to expand in the radial direction. In some cases there could be more than one set of such serpentine struts placed in a row along the length of the support frame, as shown in FIG. 27. In another form a pair of struts are connected between the serpentine struts to provide extra support to the filter membrane.

It will be understood that providing a portion of the strut with a narrowed width to facilitate bending is but one way of achieving a zone of weakness. For example, the hinges can also be formed by scored lines transverse to the strut to facilitate bending.

The distal ring 1514 of the filter frame 1510 is either slidably or fixedly mounted to the distal end 1506 of the catheter shaft. The proximal ring 1512 of the filter frame 1510 is slidably mounted along a portion of the shaft 1503 between the distal end 1506 and the balloon 1504.

The filter frame 1510 is formed from a shape memory material such as nitinol. The filter frame 1510 is heat set in the expanded shape. This normally expanded shape will cause the filter frame 1510 to bow outward if not constrained. When the filter frame 1510 expands, it draws the proximal ring 1512 distally toward the distal ring 1514. When the proximal ring 1512 is moved in a proximal direction, the filter frame 1510 will collapse.

The filter membrane 1508 of the disclosed embodiment consists of a funnel shape, but is not limited to this shape. The filter membrane 1508 is made up of semi-compliant material such as nylon or Pebax®, or could be made up of elastic materials such as thermoplastic elastomers or thermoset elastomers. Some examples of thermoset elastomers include polyurethane and copolymers (e.g., Pellathane™, Tecothane™, or Chronoflex™). These materials allow the openings in the filter material to be placed close to each other. The size of the filter openings could be 40 microns and be placed 40 microns apart. The filter membrane can also consist of a wire mesh woven such that when it opens it forms the filter screen.

The filter membrane 1508 is attached to the filter frame 1510 such that it covers the distal half of the frame. The proximal portion of the frame remains open. The filter membrane 1508 may be attached on the outside of the frame 1510 or on the inside of the frame. The filter membrane 1508 may also be attached to the mid-portion of the frame 1510 that expands the most to conform to the vessel wall, while the distal portion of the filter membrane is attached to the distal end 1506 of the catheter shaft 1503.

Because the filter frame 1510 will bow outward if not constrained, a mechanism is provided for constraining the filter frame as the device 1500 is being introduced into and withdrawn from the patient. Adjacent to the distal end of the balloon 1504, a sheath 1520 is concentrically mounted to the catheter shaft 1503. The inner wall 1522 of the sheath 1520 is spaced apart from the exterior wall of the catheter shaft 1503 to create an annular space. When at least a major portion of the filter basket 1504 has been retracted into the sheath 1520, the filter frame 1510 is constrained from expanding, thus reducing the overall diameter of the device 1500 and enabling the device to be introduced into or withdrawn from the patient.

The sheath 1520 is made of elastic material such as polyurethane or silicon rubber that will keep the filter basket 1504 collapsed as well as retrieve the filter after use when it may be filled with embolic debris. Because of this feature the catheter shaft 1503 can be built with a distal tip that has a low profile and is very flexible and hence allows true navigation through tortuous anatomy and cross through narrow passageways.

To enable manipulation of the proximal ring 1512 from a location outside of the patient to move the filter basket 1505 into and out of the sheath 1520 to expand and retract the filter 1505, an actuation wire 1526 is provided. The distal end of the actuation wire 1526 is coupled to the proximal ring 1512. From there, the actuation wire 1526 extends through a lumen 1528 along the catheter shaft 1503 to a location outside of the patient. The proximal end 1530 of the actuation wire 1526 can be manually operated by the physician, or the proximal end of the actuation wire can be coupled to a mechanical actuator that, in turn, is manipulated by the physician.

The balloon catheter 1500 is packaged and supplied with the filter basket 1505 in its normally open position so as to retain its memory. At the time of use the filter basket 1505 is retracted into the sheath 1520 by pulling on the actuation wire 1526. The catheter 1500 with filter basket 1505 retracted is tracked up to the point of treatment. The actuation wire 1526 is then pushed so that the filter basket 1505 is advanced out of the sheath 1520. As the filter basket 1505 is released from the confines of the sheath 1520, it expands to its predetermined shape and diameter. After the procedure the filter basket 1505 is retracted back into the sheath 1520 by simply pulling the actuation wire 1526.

The exact mechanism by which the filter basket 1505 collapses depends upon whether the distal ring 1514 of the filter basket is slidably or fixedly attached to the catheter shaft 1503. If the distal ring 1514 is fixed, then pulling the proximal ring 1512 in a proximal direction will draw the proximal ring away from the distal ring, place the filter ribs under tension, and collapse the filter frame 1510. This could also bring the proximal ring 1512 and part of the filter membrane 1508 into the sheath. If the distal ring 1514 is slidably mounted, then initially withdrawing the proximal ring 1512 will simply pull the distal ring along with it. However, once the proximal ring 1512 enters the sheath 1520, the filter frame 1510 will impinge upon the distal edge of the sheath and be biased inward. Further retraction of the proximal ring 1512 collapses the filter frame 1510 within the sheath 1520, as shown in FIG. 30.

Figure 36:
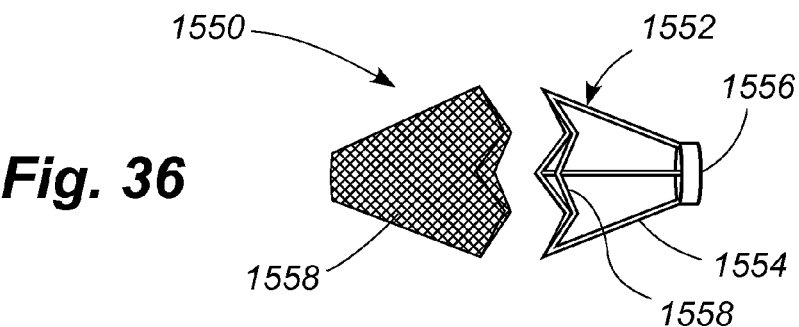
FIG. 36 is an exploded view of a filter basket according to still another embodiment.
Figure 37:
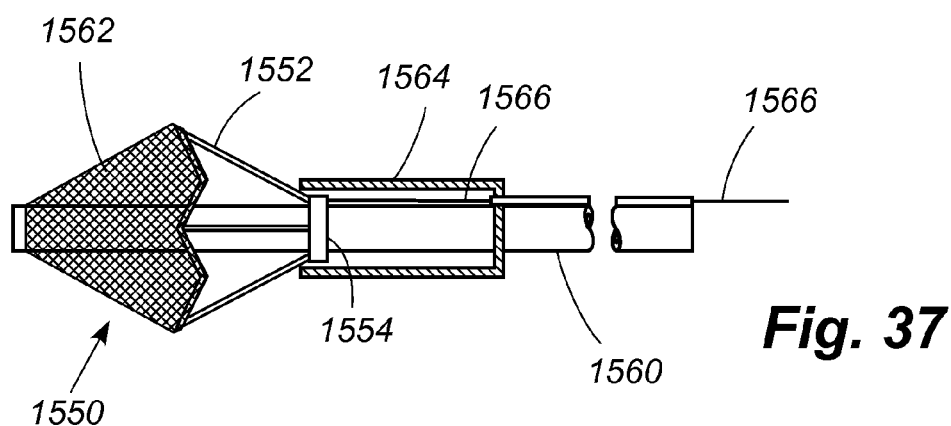
FIG. 37 is a side view of the filter basket of FIG. 37 mounted to a balloon catheter, with the filter basket expanded.
Figure 38:
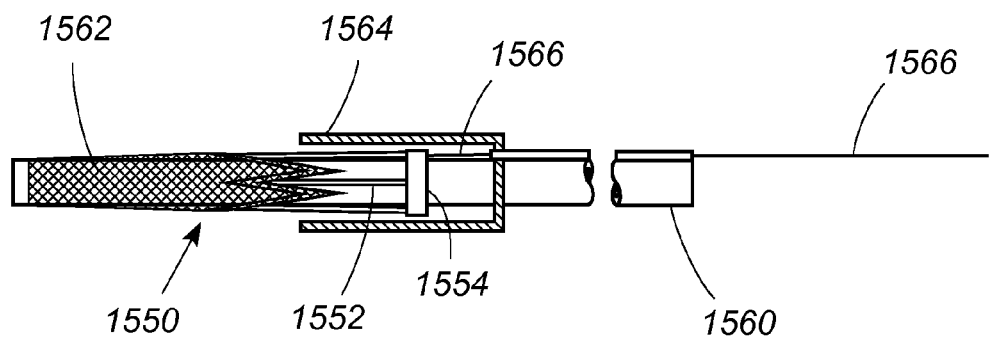
FIG. 38 is a side view of the filter basket and balloon catheter assembly of FIG. 37, with the filter basket collapsed.

A further embodiment of a filter basket 1550 is shown in FIGS. 36-38. The filter basket 1550 includes a shape memory frame 1552 without the distal half. In other words, the filter frame 1552 comprises a plurality of struts 1554 attached to a ring 1556 and extending distally and outward therefrom. The distal ends of the struts 1554 are circumferentially connected by another set of struts 1558 that forms a serpentine pattern.

The ring 1556 is slidably mounted to a catheter shaft 1560. A filter membrane 1562 is attached to the distal end of the filter frame 1552, and the other end of the filter membrane is attached to the distal portion of the catheter shaft 1560. Thus the filter frame 1552 extends only a part of the length of the filter basket 1550.

The frame 1552 is partially retracted into a sheath 1564 by means of an actuation wire 1566 to collapse the filter frame 1552, as shown in FIG. 33, to contain the captured emboli.

Figure 39:
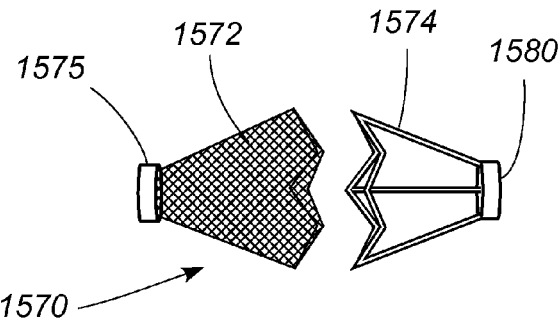
FIG. 39 is an exploded view of another embodiment of a filter basket.
Figure 40:
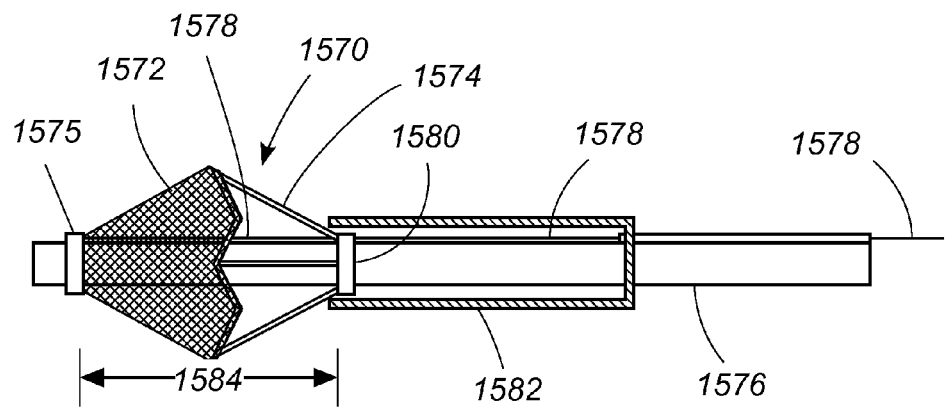
FIG. 40 is a side view of the filter basket of FIG. 39 mounted to a balloon catheter, with the filter basket expanded.
Figure 41:
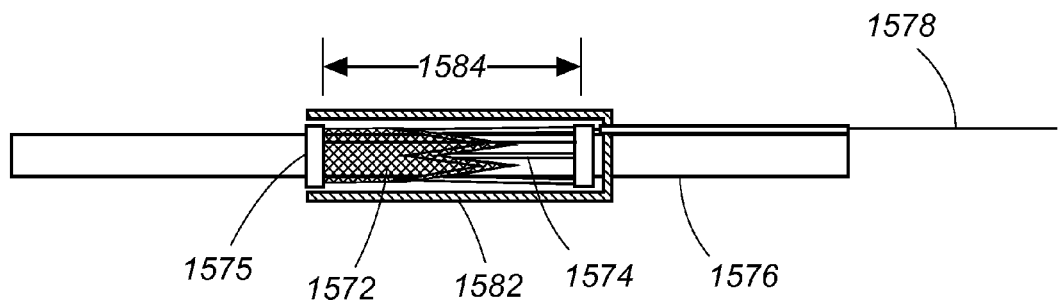
FIG. 41 is a side view of the filter basket and balloon catheter assembly of FIG. 40, with the filter basket collapsed.

FIGS. 39-41 illustrate a variation of the filter design shown in FIGS. 36-38. The filter basket 1570 is similar in most respects to the filter basket 1550 previously described. However, while the proximal end of the filter membrane 1572 is still attached to the distal end of the filter frame 1574, a distal ring 1575 is attached to the distal end of the filter membrane. The distal ring 1575 in turn is slidably attached to the distal portion of a catheter shaft 1576. The distal ring 1575 may be made up of a rigid or semi-rigid material such as a plastic or a very thin metal. An actuation wire 1578 is attached not only to the proximal ring 1580 but also extends beyond the proximal ring to attach to the distal ring 1575. Thus advancing or withdrawing the actuation wire 1578 advances or retracts not only the proximal ring 1580 but also the distal ring 1575. The filter basket 1570 is deployed by pushing the actuation wire 1578 distally, which in turn will push both the distal and proximal rings 1575, 1580 of the filter distally out of the sheath 1582 and permit the filter basket to expand to its normal shape.

The filter basket 1570 can be completely retrieved into the sheath 1582. Because the actuation wire 1578 is attached not only to a proximal ring 1580 but also extends beyond the proximal ring to attach to the distal ring 1575, the distance between the rings 1575, 1580 is fixed, as indicated by the arrows 1584. By providing a sheath 1582 having an interior length greater than the distance 1584, the entire filter basket 1570 can be retracted into the sheath.

Figure 42:
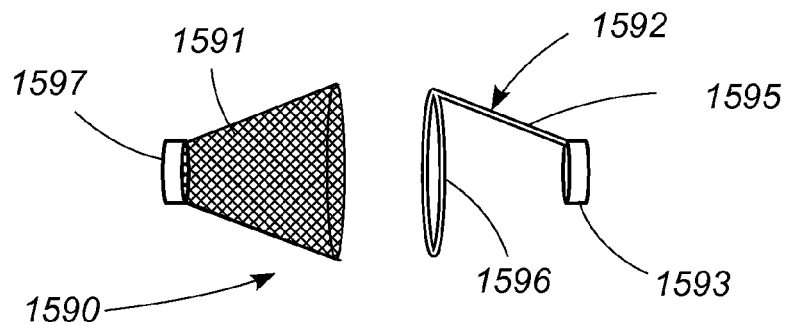
FIG. 42 is an exploded view of yet another embodiment of a filter basket.
Figure 43:
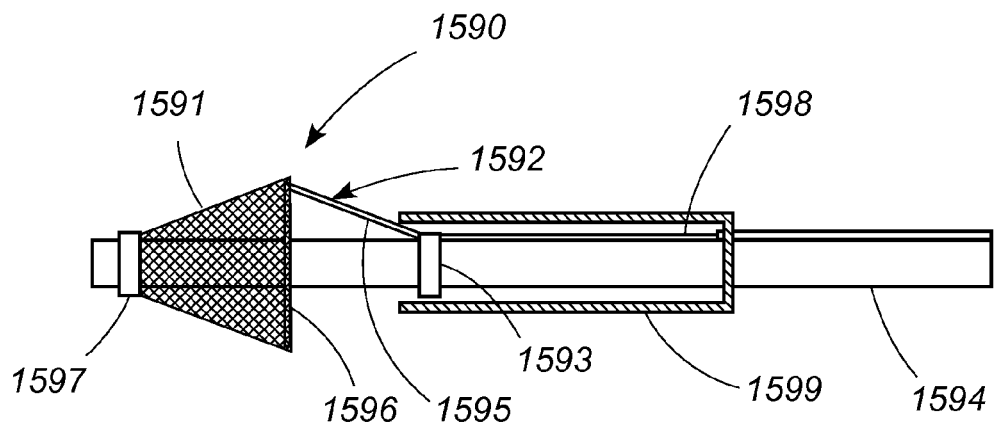
FIG. 43 is a side view of the filter basket of FIG. 42 mounted to a balloon catheter, with the filter basket expanded.
Figure 44:
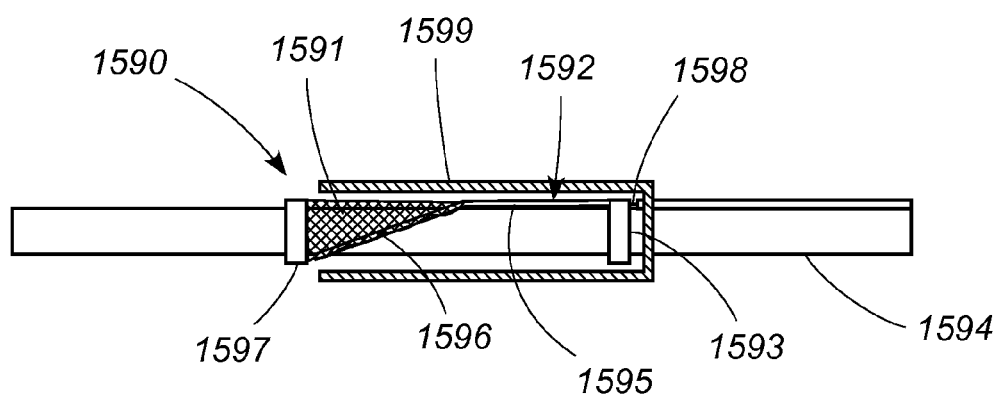
FIG. 44 is a side view of the filter basket and balloon catheter assembly of FIG. 43, with the filter basket collapsed.

FIGS. 42-44 illustrate still another embodiment of a filter basket 1590. The filter basket 1590 includes a filter membrane 1591 and a filter frame 1592. The filter frame 1592 comprises a proximal ring 1593 slidably mounted to a catheter shaft 1594. A strut 1595 extends distally from the proximal ring 1593. A loop 1596 is mounted to the strut generally coaxial with the proximal ring 1593. The filter membrane 1591 has a generally circular proximal end that attaches to the loop 1596 of the filter frame 1592. The distal end of the filter membrane 1591 is attached to a distal ring 1597.

FIG. 43 shows the filter basket 1590 in its expanded condition. The loop 1596 of the filter frame 1592 holds the filter membrane 1591 open and ready to receive embolic particles. To collapse the filter basket 1590, an actuation wire 1598 is pulled, drawing the proximal ring 1593 rearward into a sheath 1599. As the loop 1596 of the filter frame 1592 confronts the distal end of the sheath 1599, it vertically elongates, and the lower end of the loop collapses distally, as shown in FIG. 44. As the loop 1596 collapses and is drawn into the sheath 1599, the filter membrane 1591 is drawn into the sheath.

Figure 45:
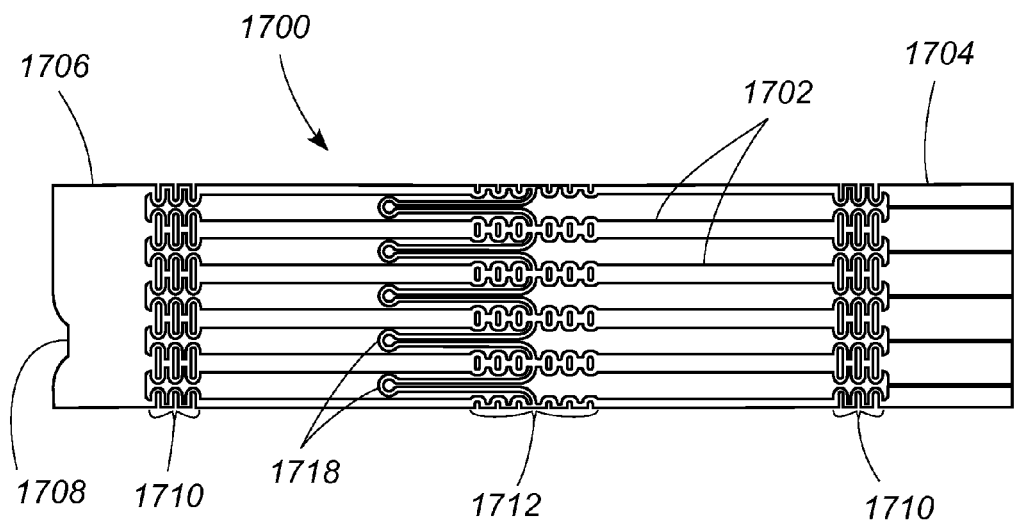
FIG. 45 is a view of another embodiment of a filter frame cut out of a flat sheet of material and before being formed into a generally cylindrical frame.
Figure 46:
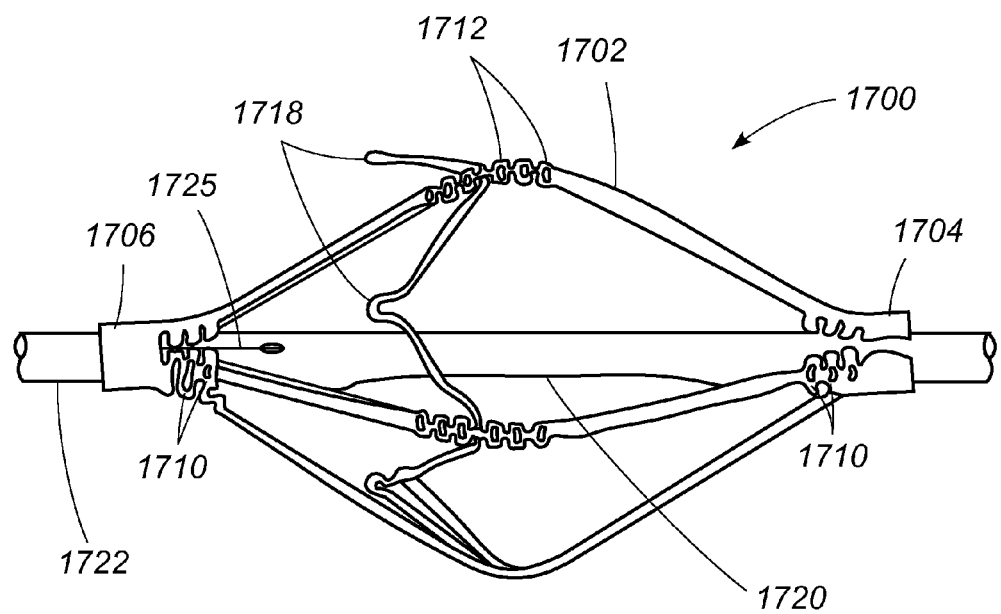
FIG. 46 is a perspective view of the filter frame of FIG. 45 formed into its generally cylindrical configuration and shown in its expanded condition.

Referring now to FIGS. 45 and 46, a frame 1700 for an embolic filter is shown. In FIG. 45 the frame is shown as a cylindrical projection, i.e., the frame is formed from a flat piece of material. The frame is then rolled into a cylinder to form the filter frame seen in FIG. 46.

The filter frame 1700 is made of a flexible material such as nitinol. The filter frame 1700 consists of five struts 1702, a proximal ring 1704, and a distal ring 1706, although a greater or lesser number of struts can be used. The struts 1702 have their proximal ends attached to the proximal ring 1704 and their distal ends attached to the distal ring 1706. The distal ring 1706 has a notch 1708 formed in it.

Figure 47:
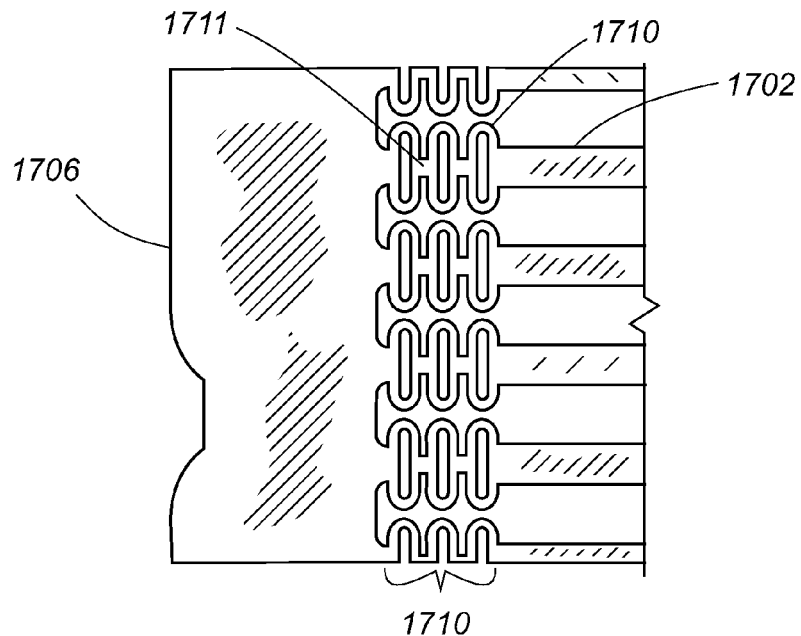
FIG. 47 is an enlarged side view of an end of the filter frame of FIG. 45.
Figure 48:
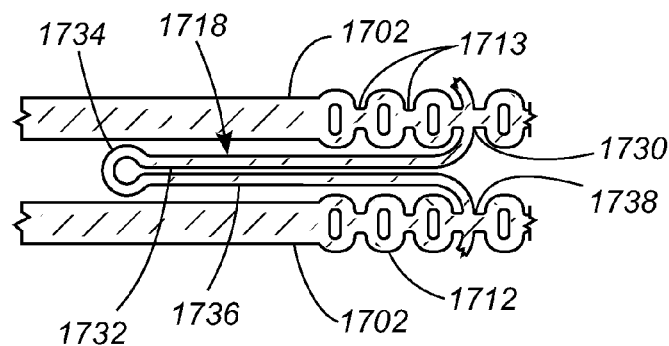
FIG. 48 is an enlarged side view of a midsection of the filter frame of FIG. 45.

Sets of oval shaped members 1710 are formed in the struts 1702 adjacent their proximal and distal ends. Adjacent oval shaped members 1710 are joined to one another by links 1711 (see FIG. 47) that are narrower in width than the struts 1702. Other groups of oval shaped members 1712 (see FIG. 48) are formed at a midsection of each of the struts 1702. Adjacent oval shaped members 1712 are also joined to one another by links 1713 that are narrower in width than the struts 1702. The oval members 1710, 1712 define elongated openings having an axis of elongation that extends generally transverse to the longitudinal axis of each strut 1702.

The use of oval shaped members 1710, 1712 inline of the struts 1702 provides several functions. First, the oval shaped members 1710, 1712 and the narrow links 1711, 1713 joining them comprise a "zone of weakness" at which the struts 1702 will naturally tend to bend, thus enabling control over the locations at which the struts deform. Second, the ovals are able to elongate, thus providing the filter frame 1700 with the ability to stretch. These features facilitate the movement of the filter frame 1700 between its collapsed and expanded positions.

Adjacent struts 1702 are radially joined by connectors 1718. The structure of the connectors 1718 can best be seen by reference to FIG. 48. Each connector 1718 comprises a first end 1730 joined to a midpoint of a first strut 1702 and extending initially toward the adjacent strut 1702. The connector then curves toward the distal ring 1706, and a first leg 1732 of the connector extends substantially parallel to the struts 1702 for a predetermined distance. The connector 1718 then forms an arcuate head 1734 portion before a second leg 1736 of the connector extends back toward the proximal ring 1704 substantially parallel to the first leg 1732. When the second leg 1736 has extended the first distance, it curves toward the adjacent strut 1702 and joins it. In the disclosed embodiment the head portion 1734 defines an arc of greater than 180°.

Figure 49:
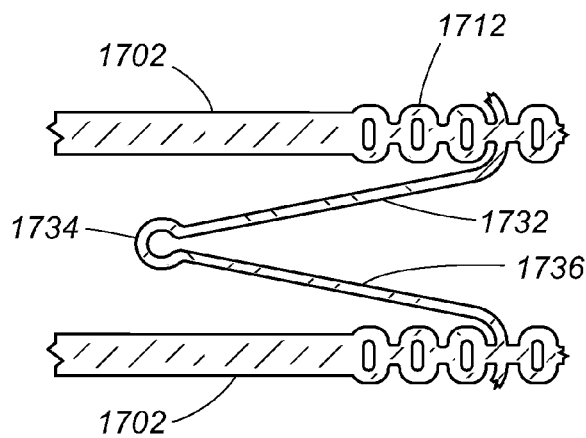
FIG. 49 is a view of the connector of FIG. 48 in an expanded configuration.

Operation of the connectors 1718 is illustrated in FIG. 49. As the two struts 1702 are spread apart, as would be the case when the actuator wire is operated, the two legs 1734, 1738 open up the arcuate portion 1736 of the connector. The arcuate portion acts as a spring such that when the actuator wire is operated, the connectors 1718 help draw adjacent struts 1702 toward one another, facilitating the collapse of the frame 1700.

A filter mesh (not shown, for clarity of illustration) overlies the distal half of the frame 1700. The proximal portion of the filter mesh is attached around its circumference to the connectors 1718 of the filter frame 1700. The distal end of the filter mesh is attached either to the catheter shaft at a point beyond the distal end of the frame, or to the distal ring 1706.

The filter frame 1700 is mounted to a portion of the shaft 1720 of a balloon catheter adjacent its distal end. The distal ring 1706 is slidably mounted for movement along the distal portion 1722 of the shaft 1720. In the disclosed embodiment the proximal ring 1704 is affixed to the shaft 1720. Alternatively the proximal ring 1704 can also be arranged to slide along the distal portion 1722 of the shaft 1720 of the balloon catheter, provided there is a hard stop to limit movement of the proximal ring 1704 of the filter frame 1700 in the proximal direction.

An actuation mechanism such as a wire 1725 or a balloon is attached to the distal ring 1706 of the filter frame 1700. In case of an actuation wire the wire could be attached within the notch 1708 provided for such an attachment.

When the actuation wire is pulled proximally or the actuation balloon inflated, the distal ring 1706 of the filter frame 1700 is drawn proximally toward the proximal ring 1704. As a result the struts 1702 of the filter frame 1700 start to expand outward from the catheter shaft. As the filter frame 1700 expands, the connecting "V" elements 1718 to open and to form a sinusoidal ring that holds the filter membrane open at its proximal end. The struts 1702 are pre-bent at the midsection ovals 1715 before assembly so that, when the actuation wire 1725 is pulled, the struts bend outward at the desired location. The bending at the midsection ovals 1715 causes the struts 1702 to protrude radially outwards. In particular, the bend is made to occur on each strut 1702 at the oval that is distal to the location where the "V" element 1718 is connected. This feature causes the filter membrane to be imposed firmly against the vessel wall and to capture efficiently any embolic particles that could be generated during the angioplasty or stent procedure.

In the embodiment of the filter frame 1700, the natural shape of the filter mesh may be in the closed position. Therefore the filter mesh would not permanently set during storage and can expand easily to the correct size.

In addition to radially supporting the filter mesh, the connectors 1718 act as springs that will assist in collapsing the filter frame once the actuation mechanism is deactivated.

An advantage of the oval members 1710, 1712 of the disclosed embodiment is that they provide a flex point to permit movement of the struts 1702 radially inward and outward while at the same time restricting lateral movement of the struts, thus preventing the filter frame 1700 from collapsing inwards during opening. Furthermore, the oval cutouts provide a mechanism by which the individual struts can elongate during expansion of the filter frame.

In each of the foregoing examples, it will be appreciated that an angioplasty balloon is but one means for relieving a stenosis in a vessel. Stents, mechanical thrombectomy devices, or other suitable apparatus may be substituted for the angioplasty balloon and positioned on the catheter at a location proximal to the embolic filter. Thus any emboli loosened by the stent or mechanical thrombectomy device will be captured by the embolic filter in the same manner as described above with respect to the angioplasty balloon.

While the foregoing disclosed embodiments comprise filter ribs of a shape memory metal such as nitinol, it will be appreciated that similar results can be obtained by using any suitable resilient material. The ribs would be formed straight, forced open by the balloon, and return to their normal shape as a result of the resiliency of the structure. Or, in the case of the embodiment of FIGS. 25 and 26, the ribs would be initially formed in an open position, deformed inwardly to fit within the outer catheter, and return to their normal open position when released from the confines of the outer catheter.

Variations in the design of the filter are also contemplated. For example, while both ends of the ribs 26 of the filter 20 are mounted to rings 22, 24, it will be appreciated that the ends of the ribs at the fixed end of the filter can be secured directly to the catheter shaft.

It will be appreciated that the disclosed devices permit the placement of the embolic filter very close to the means for treating the stenosis. This has the effect of minimizing the "landing area" of the filter and also permits the protection of side branches, as shown in FIGS. 14-17.

In the foregoing embodiments, where dimensions are given, the dimensions are for illustrative purposes only unless specifically recited in the claims below. The dimensions are intended to show general scale and proportions and, unless specifically claimed, are not intended to limit the invention to any particular size or configuration.

Finally, it will be understood that the foregoing embodiments have been disclosed by way of example, and that other modifications may occur to those skilled in the art.

What is claimed is:

1. A percutaneous transluminal angioplasty device, comprising an elongated catheter having proximal and distal ends and an outer side wall;
a treatment means attached to the catheter adjacent to the distal end thereof for treating a stenosis in a vessel;
a frame supporting an embolic filter, the frame being attached to the catheter between the treatment means and the distal end of the catheter, the frame being collapsible for insertion into a blood vessel, and the frame being expandable to an expanded position to deploy the embolic filter to capture emboli related into a bloodstream by operation of the treatment means, comprising:
a proximal ring;
a distal ring;
a plurality of longitudinally extending struts, each strut having a longitudinal axis and a width measured transverse to the longitudinal axis, wherein each strut of the plurality of struts comprises:
a proximal end attached to the proximal ring;
a distal end attached to the distal ring;
a midsection;
first, second, and third zones of weakness, each zone of weakness comprising:
a set of oval shaped members spaced along the longitudinal axis of the strut, formed in the strut, and circumscribing an oval opening, the oval opening having a long axis that is substantially transverse to the longitudinal axis of the strut; and
at least one connecting link formed in the strut and extending between adjacent oval shaped members of the zone of weakness, wherein each connecting link has a width, and the width of each connecting link is less than the width of the strut in which it is formed,
wherein the oval members of the first zone of weakness are formed in the strut adjacent the proximal end of the strut,
wherein the oval members of the second zone of weakness are formed in the strut adjacent the distal end of the strut,
wherein the oval members of the third zone of weakness are formed in the midsection of the strut, and
wherein each oval shaped member of the first, second, and third zones of weakness corresponds to a flex point that permits radial movement of its associated strut while restricting lateral movement of its associated strut,
wherein each oval shaped member is configured for longitudinal elongation to permit expansion of the frame, and
wherein the frame further comprises at least one expandable and resilient radial connector, each radial connector radially connecting two adjacent struts by attaching at a point along the third zone of weakness.

2. The percutaneous transluminal angioplasty device of claim 1, wherein the treatment means comprises an angioplasty balloon.

3. The percutaneous transluminal angioplasty device of claim 1, wherein the treatment means comprises a stent.

4. The percutaneous transluminal angioplasty device of claim 1, wherein the treatment means comprises a mechanical thrombectomy device.

5. The percutaneous transluminal angioplasty device of claim 1, wherein each of the plurality of struts are formed from a shape-memory material that urges the struts into a collapsed position.

6. The percutaneous transluminal angioplasty device of claim 5, wherein the shape-memory material comprises nitinol.

7. The percutaneous transluminal angioplasty device of claim 5, further comprising an actuator wire extending through the catheter and having proximal and distal ends, wherein the distal end of the actuator wire exits the distal end of the catheter and attaches to one of the proximal or distal rings, wherein the one of the proximal or distal rings attached to the distal end of the actuator wire is a movable ring and the one of the proximal or distal rings not attached to distal end of the actuator wire is a fixed ring, and wherein when the frame is in the collapsed position, pulling on the proximal end of the actuator wire moves the movable ring toward the fixed ring, and wherein movement of the movable ring toward the fixed ring causes the plurality of struts to expand radially outward, thereby expanding the frame to the expanded position.

8. The percutaneous transluminal angioplasty device of claim 7, wherein, when the frame is in the expanded position, releasing the proximal end of the actuator wire permits the shape-memory material of the struts to return the struts to their normal, collapsed position, collapsing the frame.

9. The percutaneous transluminal angioplasty device of claim 7, wherein the catheter further comprises an aperture in an outer side wall located between the movable ring and the fixed ring, wherein the distal end of the actuator wire exits the catheter through the aperture.

10. The percutaneous transluminal angioplasty device of claim 1, wherein each radial connector attaches two adjacent struts by extending between a connecting link of the third zone of weakness of each of the two adjacent struts.

11. The percutaneous transluminal angioplasty device of claim 10, wherein each strut of the plurality of struts is predisposed to bend radially outwardly at a bending point, wherein the bending point comprises a selected oval member of the third zone of weakness of each strut, wherein the selected oval member is positioned between the distal ring and connecting link at which a radial connector is connected to the strut.

12. The percutaneous transluminal angioplasty device of claim 1, wherein each radial connector comprises two legs and an arcuate head portion, each leg having a first end connected to one of the adjacent struts and a second end connected to an arcuate head portion.

13. The percutaneous transluminal angioplasty device of claim 12, wherein the arcuate head portion of each radial connector circumscribes an arc of greater than 180°.

14. The percutaneous transluminal angioplasty device of claim 12, wherein each radial connector is configured for radial expansion about and between a closed position and an open position, and wherein, when the plurality of radial connectors are positioned in the open position, the plurality of radial connectors cooperate to form a sinusoidal ring.

15. The percutaneous transluminal angioplasty device of claim 1, wherein a filter mesh overlies a distal portion of the struts, and wherein, in the expanded position, the struts expand radially outward, radially expanding the filter mesh.

16. The percutaneous transluminal angioplasty device of claim 15, wherein each strut of the plurality of struts is predisposed to bend radially outwardly at a bending point, wherein the bending point comprises a selected oval member of the third zone of weakness of each strut, wherein the selected oval member is positioned between the distal ring and a point at which a radial connector is connected to the strut, and wherein a proximal edge of the filter mesh is attached to the plurality of radial connectors.

* * * * *